(12) United States Patent
Chizh et al.

(10) Patent No.: US 6,846,843 B2
(45) Date of Patent: Jan. 25, 2005

(54) β-THIOAMINO ACIDS

(75) Inventors: Boris Chizh, Aachen (DE); Matthias Gerlach, Brachttal (DE); Michael Haurand, Aachen (DE); Claudia Puetz, Dueren (DE); Gero Gaube, Aachen (DE); D. Enders, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/387,843

(22) Filed: Mar. 14, 2003

(65) Prior Publication Data

US 2003/0236253 A1 Dec. 25, 2003

Related U.S. Application Data

(63) Continuation of application No. PCT/EP01/10488, filed on Sep. 11, 2001.

(30) Foreign Application Priority Data

Sep. 14, 2000 (DE) .......................................... 100 45 831
Sep. 29, 2000 (DE) .......................................... 100 49 484

(51) Int. Cl.⁷ ..................... A61K 31/195; A61K 31/38; C07C 205/00; C07D 335/00; C07D 333/22
(52) U.S. Cl. ..................... 514/562; 514/438; 514/432; 562/553; 562/556; 562/558; 562/559; 549/13; 549/28; 549/76
(58) Field of Search .................... 562/553, 556, 562/558, 559; 549/76, 13, 28; 514/562, 438, 432

(56) References Cited

U.S. PATENT DOCUMENTS

| | | | |
|---|---|---|---|
| 3,091,569 A | | 5/1963 | Sheffner |
| 4,024,175 A | | 5/1977 | Satzinger et al. |
| 4,918,223 A | | 4/1990 | Krimmer et al. |
| 4,981,873 A | | 1/1991 | Witte et al. |
| 5,401,839 A | * | 3/1995 | Au et al. .................... 536/18.7 |
| 6,225,311 B1 | * | 5/2001 | Levin et al. ............. 514/227.5 |
| 6,458,844 B2 | * | 10/2002 | Hull et al. ................... 514/599 |
| 6,620,848 B2 | * | 9/2003 | Beams et al. ............... 514/562 |
| 6,627,771 B1 | * | 9/2003 | Belliotti et al. ............. 562/553 |
| 6,642,398 B2 | * | 11/2003 | Belliotti et al. ............. 554/108 |

FOREIGN PATENT DOCUMENTS

| | | |
|---|---|---|
| CH | 534 138 | 2/1973 |
| DE | 35 10 858 A1 | 10/1985 |
| DE | 37 27 897 A1 | 3/1989 |
| DE | 38 21 540 A1 | 12/1989 |
| GB | 1191042 | 5/1970 |
| GB | 2 336 587 A | 10/1999 |
| JP | 6059399 | 3/1994 |
| WO | 00/15611 | 3/2000 |
| WO | 00/74705 A1 | 12/2000 |
| WO | 01/20336 A2 | 3/2001 |

OTHER PUBLICATIONS

Carpenter et al, CA43:8362, 1949.*

Levin et al, CA133:150908, 2000.*

* cited by examiner

*Primary Examiner*—Deborah C. Lambkin
(74) *Attorney, Agent, or Firm*—Crowell & Moring LLP

(57) ABSTRACT

Thio-alpha-amino acids of general formula (I), wherein $R^1$, $R^2$ and $R^3$ have the meanings given in the description, methods for producing them, and medicaments containing these compounds. The invention also provides methods for treating pain and other diseases using the pharmaceutical compositions comprising the thioamino acids.

35 Claims, No Drawings

β-THIOAMINO ACIDS

CROSS REFERENCE TO RELATED APPLICATIONS

The present application is a continuation of International Patent Application No. PCT/EP01/10488, filed Sep. 11, 2001, designating the United States of America and published in German as WO 02/22568, the entire disclosure of which is incorporated herein by reference. Priority is claimed based on Federal Republic of Germany Patent Application Nos. 100 45 831.9, filed Sep. 14, 2000; and 100 49 484.6, filed Sep. 29, 2000.

FIELD OF THE INVENTION

The present invention relates to β-thio-α-amino acids, process for their production, medicaments containing these compounds, and the use of thioamino acids for the production of medicaments.

BACKGROUND OF THE INVENTION

The cyclic GABA (gamma aminobutyric acid) analogue gabapentin is a clinically proven antiepileptic. Gabapentin additionally exhibits further interesting, medically relevant properties, in particular as an analgesic. New classes of structures that have an affinity for the gabapentin binding site are therefore of interest. In connection with the aforementioned medical indications there is a further need of substances that are similar in their properties to gabapentin, for example having analgesic effect.

The treatment of chronic and non-chronic pain conditions is very important in medicine. There is therefore a universal need for highly effective pain treatments. The urgent need for a patient-oriented and targeted treatment of chronic and non-chronic pain conditions, which is understood to include the successful and satisfactory treatment of pain on the part of the patient, is documented in the large number of scientific studies that have recently appeared in the field of applied analgesia and in basic research relating to nociception.

Conventional opioids such as morphine are highly effective in treating severe to extremely severe pain. Their use is however limited by the known side effects such as for example respiratory depression, vomiting, sedation, constipation and development of tolerance. Also, they are less effective in treating neuropathic or incidental pain afflicting in particular tumour patients.

DESCRIPTION OF THE INVENTION

The object of the invention was therefore to discover structures, preferably new structures, that have an affinity for the gabapentin (GBP) binding site and/or corresponding physiological activities, for example with regard to analgesia but also other GBP indications.

The invention therefore provides for the use of a β-thio-α-amino acid of formula I

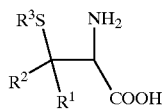

wherein $R^1$ and $R^2$ are in each case independently of one another H; $C_{1-10}$-alkyl that is branched or unbranched, saturated or unsaturated, unsubstituted or singly or multiply substituted; benzyl, aryl, $C_{3-8}$-cycloalkyl or heteroaryl, in each case unsubstituted or singly or multiply substituted; or $R^1$ and $R^2$ together form a $(CH_2)_{3-6}$ ring, saturated or unsaturated, substituted or unsubstituted, in which 0–2 C atoms may be replaced by S, O or $NR^4$,
where $R^4$ is H; or $C_{1-10}$-alkyl that is saturated or unsaturated, branched or unbranched, singly or multiply substituted, or unsubstituted;

$R^3$ is H; $C_{1-10}$-alkyl that is saturated or unsaturated, branched or unbranched, singly or multiply substituted or unsubstituted; $C_{3-8}$-cycloalkyl that is saturated or unsaturated, unsubstituted or singly or multiply substituted; aryl or heteroaryl, in each case unsubstituted or singly or multiply substituted; or aryl, $C_{3-8}$-cycloalkyl or heteroaryl bound by saturated or unsaturated $C_{1-3}$-alkyl and in each case unsubstituted or singly or multiply substituted;

in the form of their racemates, enantiomers, diastereomers, in particular mixtures of their enantiomers or diastereomers, or of an individual enantiomer or diastereomer; in the form of their physiologically compatible acidic and basic salts and/or salts with cations and/or bases or with anions and/or acids, or in the form of the free acids or bases;

with the exception of the compounds in which $R^1$, $R^2$ and $R^3$ are simultaneously H, or $R^1$ and $R^2$ are simultaneously $CH_3$ and $R^3$ corresponds to hydrogen, for the production of a medicament for the treatment of pain, in particular neuropathic, chronic or acute pain, epilepsy and/or migraine, or for the production of a medicament for the treatment of hyperalgesia and allodynia, in particular thermal hyperalgesia, mechanical hyperalgesia and allodynia and cold-induced allodynia, or inflammatory or postoperative pain, or for the production of a medicament for the treatment of hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, neurodegenerative diseases such as Alzheimer's disease, Huntington's disease, Parkinson's disease and epilepsy; gastrointestinal lesions; erythromelalgic or post-poliomyelitic pain, trigeminal or post-herpes neuralgia; or as an anticonvulsant, analgesic or anxiolytic.

These substances bind to the gabapentin binding site and exhibit a pronounced analgesic action.

Within the context of the present invention, alkyl radicals and cycloalkyl radicals are understood to be saturated or unsaturated (but not aromatic), branched, unbranched or cyclic hydrocarbons that may be unsubstituted or singly or multiply substituted. In this connection $C_{1-2}$-alkyl denotes $C_1$- or $C_2$-alkyl, $C_{1-3}$-alkyl denotes $C_1$-, $C_2$- or $C_3$-alkyl, $C_{1-4}$-alkyl denotes $C_1$-, $C_2$-, $C_3$- or $C_4$-alkyl, $C_{1-5}$-alkyl denotes $C_1$-, $C_2$-, $C_3$-, $C_4$ or $C_5$-alkyl, $C_{1-6}$-alkyl denotes $C_1$-, $C_2$-, $C_3$-, $C_4$-, $C_5$- or $C_6$-alkyl, $C_{1-7}$-alkyl denotes $C_1$-, $C_2$-, $C_3$-, $C_4$-, $C_5$-, $C_6$- or $C_7$-alkyl, $C_{1-8}$-alkyl denotes $C_1$-, $C_2$-, $C_3$-, $C_4$-, $C_5$-, $C_6$-, $C_7$ or $C_8$-alkyl, $C_{1-10}$-alkyl denote $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl denotes $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. In addition $C_{3-4}$-cycloalkyl denotes $C_3$- or $C_4$-cycloalkyl, $C_{3-5}$-cycloalkyl denotes $C_3$-, $C_4$- or $C_5$-cycloalkyl, $C_{3-6}$cycloalkyl denotes $C_3$-, $C_4$-, $C_5$- or $C_6$-cycloalkyl, $C_{3-7}$-cycloalkyl denotes $C_3$-, $C_4$-, $C_5$-, $C_6$- or $C_7$-cycloalkyl, $C_{3-8}$-cycloalkyl denotes $C_3$-, $C_4$-, $C_5$-, $C_6$-, $C_7$- or $C_8$-cycloalkyl, $C_{4-5}$-cycloalkyl denotes $C_4$- or $C_5$-cycloalkyl, $C_{4-6}$-cycloalkyl denotes $C_4$-, $C_5$- or $C_6$-cycloalkyl, $C_{4-7}$cycloalkyl denotes $C_4$-, $C_5$-, $C_6$- or $C_7$-cycloalkyl, $C_{5-6}$-cycloalkyl denotes $C_5$- or $C_6$-cycloalkyl and $C_{5-7}$-cycloalkyl denotes $C_5$-, $C_6$- or $C_7$-cycloalkyl. With regard to cycloalkyl, the term also includes saturated cycloalkyls in which 1 or 2 carbon atoms are replaced by a heteroatom, i.e. S, N or O. The term cycloalkyl also includes in particular singly or multiply, preferably singly, unsaturated cycloalkyls without a heteroatom in the ring as long as the cycloalkyl does not form an aromatic system. The alkyl or cycloalkyl radicals are preferably methyl, ethyl, vinyl (ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

In connection with alkyl and cycloalkyl, the term "substituted" within the context of the present invention is understood to mean the replacement of an hydrogen atom by F, Cl, Br, I, $NH_2$, SH or OH, and the expression "multiply substituted" radicals is understood to mean that the substitution takes place multiply with the same or different substituents on different as well as on the same atoms, for example triple substitution on the same C atom as in the case of $CF_3$ or at different positions as in the case of —CH(OH)—CH=CH—$CHCl_2$. Particularly preferred substituents in this connection are F, Cl and OH.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, etc.

The term aryl radical is understood to mean ring systems with at least one aromatic ring but without heteroatoms in the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring, which contain one or more heteroatoms from the group comprising nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In this connection the term substituted in connection with aryl and heteroaryl is understood to denote the substitution of the aryl or heteroaryl with $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this connection the radical $R^{23}$ denotes H, a $C_{1-10}$-alkyl radical, preferably a $C_{1-6}$-alkyl radical, an aryl or heteroaryl radical or an aryl or heteroaryl radical bonded via a $C_{1-3}$-alkylene group, wherein these aryl and heteroaryl radicals may not themselves be substituted by aryl or heteroaryl radicals, the radicals $R^{24}$ and $R^{25}$, which are identical or different, denote H, a $C_{1-10}$-alkyl radical, preferably a $C_{1-6}$-alkyl radical, an aryl radical, a heteroaryl radical or an aryl or heteroaryl radical bonded via a $C_{1-3}$-alkylene group, wherein these aryl and heteroaryl radicals may not themselves be substituted by aryl or heteroaryl radicals, or the radicals $R^{24}$ and $R^{25}$ together denote $CH_2CH_2OCH_2CH_2$, $CH_2CH_2NR^{26}CH_2CH_2$, or $(CH_2)_{3-6}$, and the radical $R^{26}$ denotes H, a $C_{1-10}$-alkyl radical, preferably a $C_{1-6}$-alkyl radical, an aryl or heteroaryl radical, or an aryl or heteroaryl radical bonded via a $C_{1-3}$-alkylene group, wherein these aryl and heteroaryl radicals may not themselves be substituted with aryl or heteroaryl radicals.

The term salt is understood to mean any form of the active constituent according to the invention in which this adopts an ionic form or is charged and is coupled to a counterion (a cation or anion), and is present in solution. The term is also understood to include complexes of the active constituent with other molecules and ions, in particular via ionic interactions.

The term physiologically compatible salt with cations or bases is understood within the context of the present invention to mean salts of at least one of the compounds according to the invention—generally of a (deprotonated) acid—as an anion of at least one, preferably inorganic cation, that are physiologically compatible, especially when used in humans and/or mammals. Particularly preferred are the salts of alkali and alkaline earth metals, but also with $NH_4^+$, and in particular (mono) or (di)sodium, (mono) or (di)potassium, magnesium or calcium salts.

The term physiologically compatible salt with anions or acids is understood within the context of the present invention to mean salts of at least one of the compounds according to the invention—generally protonated, for example on the nitrogen atom—as a cation with at least one anion, that are physiologically compatible, especially when used in humans and/or mammals. In the context of the present invention the term is particularly understood to denote the salt formed with a physiologically compatible acid, namely salts of the respective active constituent with inorganic or organic acids, that are physiologically compatible, especially when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

All the substances listed hereinbefore and specified for use displace gabapentin from its binding site, which has also not yet been experimentally determined. This implies however that the substances according to the invention bind at the same binding site and act physiologically via the latter, presumably with the same action profile as gabapentin. This assumption that the same action is also exerted at the same binding site is demonstrated by the analgesic effect. Thus, the compounds according to the invention not only displace gabapentin from its binding site but—like gabapentin—also have a marked analgesic effect. Accordingly, the invention provides for the use of the aforementioned and defined thioamino acids in the previously mentioned medical indications in which gabapentin is active, i.e. in particular for the treatment of pain, epilepsy or migraine, but specifically also for the treatment of neuropathic pain including hyperalgesia and allodynia, and other conditions for which gabapentin is indicated for use.

Gabapentin is a known antiepileptic having an anticonvulsive action. In addition to this gabapentin is also used in various other medical indications, and inter alia is prescribed by physicians for the treatment of migraine and bipolar disorders as well as hot flushes (e.g. in the post menopause) (M. Schrope, Modern Drug Discovery, September 2000, p. 11). Other medical indications in which gabapentin exhibits a therapeutic potential have been identified in human studies and in clinical practice (J. S. Bryans, D. J. Wustrow; "3-Substituted GABA Analogs with Central Nervous System Activity: A Review" in Med. Res. Rev. (1999), pp. 149–177). The action of gabapentin is listed in detail in this review article. For example, gabapentin is effective in the treatment of chronic pain and behavioral disturbances. In particular the following properties of gabapentin are listed: anticonvulsive and antiepileptic actions, the use to treat chronic, neuropathic pain, in particular thermal hyperalgesia, mechanical allodynia, and cold-induced allodynia. In addition gabapentin is effective against neuropathy triggered by nerve damage, and in particular is also successful in treating neuropathic pain as well as inflammatory and post-operative pain. Gabapentin is also successful as an antipsychotic agent, in particular as an anxiolytic. Further proven indications for use include: amyotrophic lateral sclerosis (ALS), reflex sympathetic dystrophy (RSD), spastic palsy, restless leg syndrome, treatment of symptoms and pain caused by multiple sclerosis, acquired nystagmus, treatment of the symptoms of Parkinson's disease, painful diabetic neuropathy, and psychiatric disorders, for example bipolar disorders, mood fluctuations, and manic behavior. Gabapentin has also been successfully used to treat erythromelalgic pain, post-poliomyelitic pain, trigeminal neuralgia and post-treatment neuralgia (Bryans and Wustrow (1999), etc.). The general efficacy of gabapentin in neurodegenerative conditions is generally known and is also demonstrated by the examples given in the aforementioned review article. Such neurodegenerative conditions include Alzheimer's disease, Huntington's disease, Parkinson's disease and epilepsy. The effectiveness of gabapentin in gastrointestinal disorders is also known.

In a preferred embodiment a thioamino acid according to formula I is used in these medical indications, wherein $R^1$ and $R^2$ are in each case independently of one another $C_{1-10}$-alkyl that is branched or unbranched, saturated or unsaturated, unsubstituted or singly or multiply substituted; benzyl, aryl, $C_{3-8}$-cycloalkyl or heteroaryl, in each case unsubstituted or singly or multiply substituted; or $R^1$ and $R^2$ together form a $(CH_2)_{3-6}$ ring, saturated or unsaturated, substituted or unsubstituted, in which 0–2 C atoms may be replaced by S, O or $NR^4$.

In a further preferred embodiment a thioamino acid according to formula I is used in these medical indications, wherein $R^1$ and $R^2$ are in each case independently of one another H; $C_{1-10}$-alkyl that is branched or unbranched, saturated or unsaturated, unsubstituted or singly or multiply substituted; phenyl or thiophenyl, in each case unsubstituted or singly substituted (preferably with $OCH_3$, $CH_3$, OH, SH, $CF_3$, F, Cl, Br or I); or $C_{3-8}$-cycloalkyl that is unsubstituted or substituted, or $R^1$ and $R^2$ together form a $(CH_2)_{3-6}$ ring that is substituted or unsubstituted, in which 0–1 C atoms may be replaced by S, O or $NR^4$, preferably one of the radicals $R^1$ and $R^2$ denotes $C_{1-2}$-alkyl, in particular methyl or ethyl, that is in each case unsubstituted or singly or multiply substituted; or denotes phenyl, thiophenyl, in each case unsubstituted or singly substituted (preferably with $OCH_3$, $CH_3$, OH, SH, $CF_3$, F, Cl, Br or I); or denotes $C_{3-8}$-cycloalkyl that is unsubstituted or singly substituted; and the other of the radicals $R^1$ and $R^2$ denotes $C_{2-10}$-alkyl, in particular ethyl, n-propyl, i-propyl, n-butyl, i-butyl, tert.-butyl, pentyl, hexyl, heptyl or octyl, which is branched or unbranched, saturated or unsaturated, unsubstituted or singly or multiply substituted; or denotes phenyl or thiophenyl, in each case unsubstituted or singly substituted (preferably with $OCH_3$, $CH_3$, OH, SH, $CF_3$, F, Cl, Br or I); or denotes $C_{3-8}$-cycloalkyl, in particular cyclopropyl, cyclobutyl, cyclopentyl, cyclohexyl or cycloheptyl, in each case unsubstituted or singly substituted, or $R^1$ and $R^2$ together form cyclopropyl, cyclobutyl, cyclopentyl, cyclohexyl or cycloheptyl, in particular cyclopropyl, cyclobutyl or cyclopentyl, in each case unsubstituted or singly substituted, in which a C atom in the ring is optionally replaced by S.

In another preferred embodiment, a thioamino acid according to formula I is used in these medical indications, wherein $R_3$ is selected from H; $C_{1-6}$-alkyl that is saturated or unsaturated, branched or unbranched, singly or multiply substituted or unsubstituted; phenyl or thiophenyl that is unsubstituted or singly substituted (preferably with $OCH_3$, $CH_3$, OH, SH, $CF_3$, F, Cl, Br or I); or phenyl bound via $CH_3$, that is unsubstituted or singly substituted (preferably with $OCH_3$, $CH_3$, OH, SH, $CF_3$, F, Cl, Br or I); preferably $R^3$ is selected from H; $C_{1-6}$-alkyl that is saturated, unbranched and unsubstituted, in particular methyl, ethyl, propyl, n-propyl, i-propyl, butyl, n-butyl, i-butyl, tert.-butyl, pentyl or hexyl; phenyl or thiophenyl that is unsubstituted or singly substituted (preferably by $OCH_3$, $CH_3$, OH, SH, $CF_3$, F, Cl, Br or I); or phenyl bound via $CH_3$, and that is unsubstituted or singly substituted (preferably with $OCH_3$, $CH_3$, OH, SH, $CF_3$, F, Cl, Br or I).

It is furthermore preferred if, for the use according to the invention, the following applies to the thioamino acid according to formula I that is used:

if one of $R^1$ or $R^2$ is hydrogen and $R^3$ is benzyl or H, the other of $R^1$ or $R^2$ may not be phenyl, if $R^1$ and $R^2$ together form cyclopentyl, $R^3$ may not be H, if one of $R^1$ or $R^2$ is hydrogen and the other of $R^1$ or $R^2$ is phenyl, $R^3$ may not be substituted or unsubstituted benzyl, or if one of $R^1$ or $R^2$ is hydrogen and the other of $R^1$ or $R^2$ is methyl, $R^3$ may not be H.

In a further preferred embodiment of the invention a thioamino acid selected from the following group is used:

2-amino-3-mercapto-3-methylpentanoic acid 2-amino-3-mercapto-3-methylhexanoic acid 2-amino-3-mercapto-3-methylheptanoic acid
2-amino-3-mercapto-3-methyloctanoic acid
2-amino-3-mercapto-3-methylnonanoic acid
2-amino-3-mercapto-3-methyldecanoic acid
2-amino-3-ethyl-3-mercaptopentanoic acid
amino-(1-mercaptocyclopentyl)acetic acid
amino-3-ethyl-3-mercaptohexanoic acid
2-amino-3-mercapto-3-methyldecanoic acid
2-amino-3-mercapto-3-methylnonanoic acid
2-amino-3-mercapto-3-methyloctanoic acid
2-amino-3-ethylsulfanyl-3-methyloctanoic acid
2-amino-3-benzylsulfanyl-3-methyloctanoic acid
2-amino-3-mercapto-3-propyl-3-hexanoic acid
amino-(1-mercaptocycloheptyl)acetic acid
2-amino-3-mercapto-3-propyl-3-hexanoic acid
amino-(1-mercaptocycloheptyl)acetic acid
2-amino-3-ethylsulfanyl-3-methylnonanoic acid
2-amino-3-methyl-3-propylsulfanylnonanoic acid
2-amino-3-hexylsulfanyl-3-methylnonanoic acid
2-amino-3-benzylsulfanyl-3-methylnonanoic acid
2-amino-3-benzylsulfanyl-3-methyldecanoic acid
2-amino-3-ethylsulfanyl-3-methyldecanoic acid
2-amino-3-cyclopropyl-3-(4-fluorophenyl)-3-mercaptopropanoic acid
2-amino-3-cyclopropyl-3-mercaptobutanoic acid
2-amino-3-cyclobutyl-3-mercaptobutanoic acid
2-amino-3-cyclohexyl-3-mercaptobutanoic acid
2-amino-3-mercapto-3-thiophen-2-yl-butanoic acid
2-amino-3-ethyl-3-mercaptoheptanoic acid
amino-(1-mercaptocyclohexyl)-ethanoic acid
amino-(1-mercapto-3-methylcyclohexyl)-ethanoic acid
amino-(1-mercapto-2-methylcyclohexyl)-ethanoic acid
amino-(1-mercapto-4-methylcyclohexyl)-ethanoic acid
amino-(4-mercaptotetrahydrothiopyran-4-yl)-ethanoic acid
2-amino-3-mercapto-3,4-dimethylpentanoic acid, and
2-amino-3-mercapto-3,4-dimethylhexanoic acid
in the form of their racemates, enantiomers, diastereomers, in particular mixtures of their enantiomers or diastereomers, or of an individual enantiomer or diastereomer; in the form of their physiologically compatible acidic and basic salts or salts with cations and/or bases or with anions or acids or in the form of the free acids or bases, preferably in the form of the hydrochloride.

It is furthermore preferred if in the use according to the invention at least one thioamino acid used is present as pure diastereomer and/or enantiomer, as racemate or as a non-equimolar or equimolar mixture of the diastereomers and/or enantiomers.

The invention furthermore provides β-thio-α-amino acids of formula I

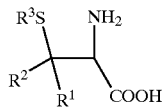

I wherein
one of the radicals $R^1$ and $R^2$ denotes $C_{1-6}$-alkyl that is saturated or unsaturated, branched or unbranched, singly or multiply substituted or unsubstituted; and the other of the radicals $R^1$ and $R^2$ denotes $C_{3-10}$-alkyl that is saturated or unsaturated, branched or unbranched, singly or multiply substituted or unsubstituted; or denotes phenyl, thiophenyl or $C_{3-8}$-cycloalkyl, in each case unsubstituted or singly or multiply substituted, and
$R^3$ is H; $C_{1-10}$-alkyl that is saturated or unsaturated, branched or unbranched, singly or multiply substituted, or unsubstituted; $C_{3-8}$-cycloalkyl that is saturated or unsaturated, unsubstituted or singly or multiply substituted; aryl or heteroaryl, in each case unsubstituted or singly or multiply substituted; or aryl, $C_{3-8}$-cycloalkyl or heteroaryl bound via saturated or unsaturated $C_{1-3}$-alkyl, in each case unsubstituted or singly or multiply substituted,
in the form of their racemates; enantiomers, diastereomers, in particular mixtures of their enantiomers or diastereomers, or of an individual enantiomer or diastereomer; in the form of their physiologically compatible acidic and basic salts or salts with cations or bases or with anions or acids, or in the form of the free acids or bases.

A preferred embodiment of the invention is a thioamino acid according to the invention wherein
one of the radicals $R^1$ and $R^2$ denotes $C_{1-2}$-alkyl that is singly or multiply substituted or unsubstituted, in particular methyl or ethyl, and the other of the radicals $R^1$ and $R^2$ denotes $C_{3-10}$-alkyl, preferably $C_{3-8}$-alkyl, that is saturated or unsaturated, branched or unbranched, singly or multiply substituted or unsubstituted, in particular propyl, n-propyl, i-propyl, butyl, n-butyl, i-butyl, tert.-butyl, pentyl, hexyl, heptyl or octyl; or phenyl or thiophenyl, in each case unsubstituted or singly substituted, (preferably with $OCH_3$, $CH_3$, OH, SH, $CF_3$, F, Cl, Br or I); or cyclopropyl, cyclobutyl, cyclopentyl, cyclohexyl or cycloheptyl.

A preferred embodiment of the invention is a thioamino acid according to the invention wherein
$R_3$ is H; $C_{1-6}$-alkyl that is saturated or unsaturated, branched or unbranched, singly or multiply substituted, or unsubstituted; phenyl or thiophenyl that is unsubstituted or singly substituted (preferably with $OCH_3$, $CH_3$, OH, SH, $CF_3$, F, Cl, Br or I); or phenyl bonded via saturated $CH_3$ and that is unsubstituted or singly substituted (preferably with $OCH_3$, $CH_3$, OH, SH, $CF_3$, F, Cl, Br or I); and $R^3$ is H; $C_{1-6}$-alkyl that is saturated, unbranched and unsubstituted, in particular methyl, ethyl, propyl, n-propyl, i-propyl, butyl, n-butyl, i-butyl, tert.-butyl, pentyl or hexyl; phenyl or thiophenyl that is unsubstituted or singly substituted (preferably by $OCH_3$, $CH_3$, OH, SH, $CF_3$, F, Cl, Br or I); or phenyl bound via saturated $CH_3$, and that is unsubstituted or singly substituted (preferably with $OCH_3$, $CH_3$, OH, SH, $CF_3$, F, Cl, Br or I).

In a particularly preferred embodiment of the invention the thioamino acid according to the invention is:
2-amino-3-mercapto-3-methylhexanoic acid
2-amino-3-mercapto-3-methylheptanoic acid
2-amino-3-mercapto-3-methyloctanoic acid
2-amino-3-mercapto-3-methylnonanoic acid
2-amino-3-mercapto-3-methyldecanoic acid
amino-3-ethyl-3-mercaptohexanoic acid
2-amino-3-mercapto-3-methyldecanoic acid 2-amino-3-mercapto-3-methylnonanoic acid
2-amino-3-mercapto-3-methyloctanoic acid
2-amino-3-ethylsulfanyl-3-methyloctanoic acid
2-amino-3-benzylsulfanyl-3-methyloctanoic acid
2-amino-3-mercapto-3-propyl-3-hexanoic acid
amino-(1-mercaptocycloheptyl)acetic acid
2-amino-3-mercapto-3-propyl-3-hexanoic acid
2-amino-3-ethylsulfanyl-3-methylnonanoic acid
2-amino-3-methyl-3-propylsulfanylnonanoic acid
2-amino-3-hexylsulfanyl-3-methylnonanoic acid
2-amino-3-benzylsulfanyl-3-methylnonanoic acid
2-amino-3-benzylsulfanyl-3-methyldecanoic acid
2-amino-3-ethylsulfanyl-3-methyldecanoic acid
2-amino-3-cyclopropyl-3-mercaptobutanoic acid
2-amino-3-cyclobutyl-3-mercaptobutanoic acid
2-amino-3-cyclohexyl-3-mercaptobutanoic acid
2-amino-3-mercapto-3-thiophen-2-yl-butanoic acid
2-amino-3-ethyl-3-mercaptoheptanoic acid
2-amino-3-mercapto-3,4-dimethylpentanoic acid, or
2-amino-3-mercapto-3,4-dimethylhexanoic acid in the form of their racemates; enantiomers, diastereomers, in particular mixtures of their enantiomers or diastereomers, or of an individual enantiomer or diastereomer; in the form of their physiologically compatible acidic and basic salts or salts with cations or bases or with anions or acids, or in the form of the free acids or bases, preferably in the form of the hydrochloride.

The substances according to the invention are toxicologically harmless, with the result that they are suitable for use as pharmaceutical active constituents in medicaments. The invention therefore also provides medicaments or pharmaceutical compositions containing at least one thioamino acid according to the invention, as well as optionally suitable additives and/or auxiliary substances and/or optionally further active constituents.

The medicaments according to the invention contain, apart from at least one substituted thioamino acid according to the invention, optionally suitable additives and/or auxiliary substances, i.e. carrier materials, fillers, solvents, diluents, dyes and/or binders, and may be administered as liquid medicament forms in the form of injection solutions, drops or juices, or as semi-solid medicament forms in the form of granules, tablets, pellets, patches, capsules, plasters or aerosols. The choice of the auxiliary substances, etc., as well as the amounts thereof to be used depend on whether the medicament is to be administered orally, perorally, parenterally, intravenously, intraperitoneally, intradermally, intramuscularly, intranasally, buccally, rectally or topically, for example to the skin, the mucous membranes or the eyes. For oral administration, preparations in the form of tablets, sugar-coated pills, capsules, granules, drops, juices and syrups are suitable, while for parenteral, topical and inhalative application, solutions, suspensions, readily reconstitutable dry preparations as well as sprays are suitable. Thioamino acids according to the invention in a depôt form, in dissolved form or in a plaster, optionally with the addition of agents promoting skin penetration, are suitable percutaneous application preparations. Orally or percutaneously usable preparation forms may provide for a delayed release of the thioamino acids according to the invention. In principle further active constituents known to the person skilled in the art may be added to the medicaments according to the invention.

The amount of active constituent to be administered to the patient varies depending on the patient's weight, type of application, medical indication for use and the severity of the condition. Normally 0.005 to 1000 mg/kg body weight, preferably 0.05 to 5 mg/kg of at least one thioamino acid according to the invention are applied.

In a preferred form of the medicament, a thioamino acid according to the invention is present as a pure diastereomer and/or enantiomer, as a racemate, or as a non-equimolar or equimolar mixture of the diastereomers and/or enantiomers.

In this connection it may be preferred if a thioamino acid according to the invention is present as a pure diastereomer and/or enantiomer, as a racemate, or as a non-equimolar or equimolar mixture of the diastereomers and/or enantiomers.

The invention also provides a process for treating a person or non-human mammal that requires treatment of medically relevant symptoms by administration of a therapeutically effective dose of a thioamino acid mentioned hereinbefore, preferably according to the invention or used according to the invention, or of a medicament according to the invention. The invention relates in particular to suitable processes for treating pain, in particular neuropathic, chronic or acute pain, including migraine, hyperalgesia and allodynia, especially thermal hyperalgesia, mechanical hyperalgesia and allodynia and cold-induced allodynia, or for treating inflammatory or post-operative pain, epilepsy, hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, neurodegenerative diseases such as Alzheimer's disease, Huntington's disease, Parkinson's disease and epilepsy; erythromelalgic or post-poliomyelitic pain, trigeminal or post-herpes neuralgia.

The invention also provides a process for producing a thioamino acid according to the invention in a form as described hereinafter.

General Process for Producing the Substituted β-thio-α-amino Acids

Reaction scheme 1:

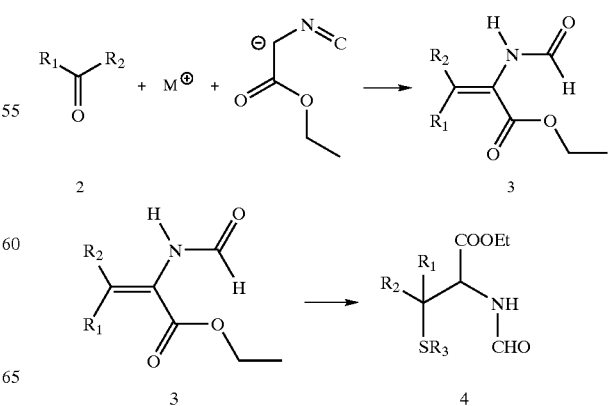

-continued

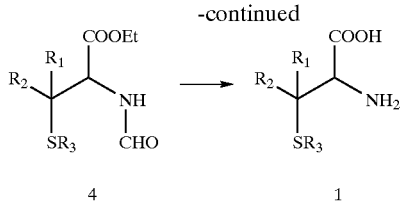

Deprotonation of the isocyanoacetic acid ethyl ester with bases such as butyllithium, sodium hydride or potassium tert.-butylate followed by reaction with ketones of formula 2 in tetrahydrofuran leads to (E,Z)-2-formylaminoacrylic acid ethyl esters of the general formula 3. By reacting (E,Z)-2-formylaminoacrylic acid ethyl esters of formula 3 with $P_4S_{10}$ in toluene or with mercaptans of the general formula $R_3SH$ in the presence of butyllithium in toluene, formylamino ethyl esters of formula 4 are obtained. Reaction of the formylamino ethyl esters of formula 4 with hydrochloric acid leads to the thioamino acids of formula 1. The separation of the diastereomers is carried out at a suitable stage by means of HPLC, column chromatography or crystallization. Separation of the enantiomers is carried out in the final stage, likewise by means of HPLC, column chromatography or crystallization. The amino acids of formula 1 are obtained according to this process as hydrochlorides. Further salt forms are obtained by release of the base or reprecipitation by conventional methods.

The invention accordingly provides a process for the production of a thioamino acid according to the invention by the following steps:

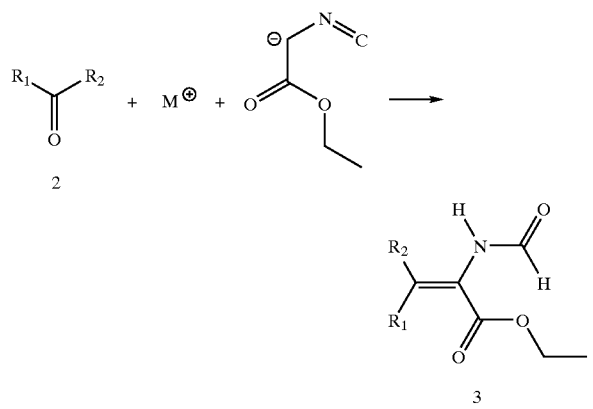

Deprotonation of the isocyanoacetic acid ethyl ester with bases, preferably butyllithium, sodium hydride or potassium tert.-butylate followed by reaction with ketones of formula 2 in tetrahydrofuran leads to (E,Z)-2-formylaminoacrylic acid ethyl esters of formula 3,

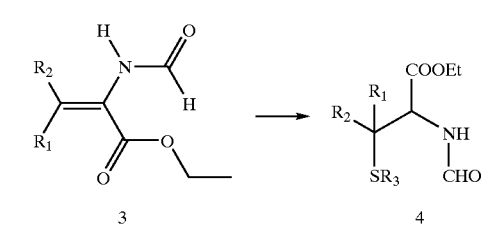

reaction of (E,Z)-2-formylaminoacrylic acid ethyl esters of formula 3 with $P_4S_{10}$ in toluene or with mercaptans of formula $R_3SH$ in the presence of butyllithium in toluene, which leads to formylamino ethyl esters of formula 4

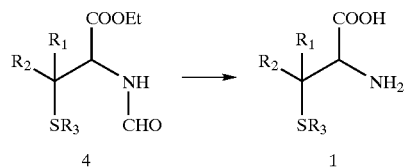

reaction of the formylamino ethyl esters of formula 4 with acid, preferably hydrochloric acid, which leads to the thioamino acids of formula 1 or I according to one of claims 1 to 4, optionally followed or interrupted by separation of the diastereomers at a suitable stage by means of HPLC, column chromatography or crystallisation, or followed by separation of the enantiomers by means of HPLC, column chromatography or crystallisation, wherein R1 to R3 have the meanings already mentioned above or correspond to a corresponding radical protected with a suitable protective group.

Salt Formation

The compounds of the formula I can be converted into their salts by a method well-known to those ordinarily skilled in the art, using physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The salt formation is preferably carried out in a solvent, for example diethyl ether, diisopropyl ether, alkyl esters of acetic acid, acetone and/or 2-butanone, or water. For the production of the hydrochlorides, trimethylchlorosilane in aqueous solution is suitable. It is also possible to carry out the conversion into basic salts using metal ions, e.g. alkali metal and alkaline earth metal ions.

The invention is described in more detail hereinafter by means of examples, without however being restricted thereto.

EXAMPLES

The following examples illustrate compounds according to the invention, their preparation, and effectiveness investigations carried out using these compounds.

The following details apply in general:

The chemicals and solvents used were commercially obtained from customary suppliers (Acros, Avocado, Aldrich, Fluka, Lancaster, Maybridge, Merck, Sigma, TCI etc. or were synthesized).

The analysis was carried out by ESI mass spectrometry or HPLC.

Syntheses:

Example 1

Synthesized compounds:

Representative examples of compounds according to the invention are the following compounds:

Compound 1)

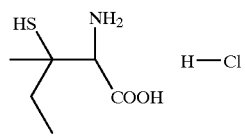

rac-2-amino-3-mercapto-3-methylpentanoic acid hydrochloride as a 7:3 threo/erythro mixture Compound 2)

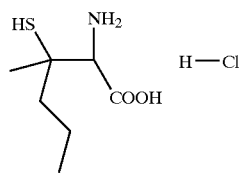

rac-2-amino-3-mercapto-3-methylhexanoic acid hydrochloride as a 7:3 threo/erythro mixture Compound 3)

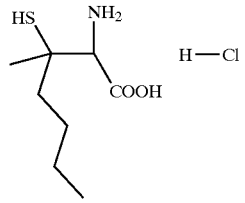

rac-2-amino-3-mercapto-3-methylheptanoic acid hydrochloride as a 6:4 threo/erythro mixture Compound 4)

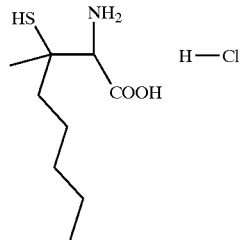

rac-2-amino-3-mercapto-3-methyloctanoic acid hydrochloride as a 1:1 threo/erythro mixture Compound 5)

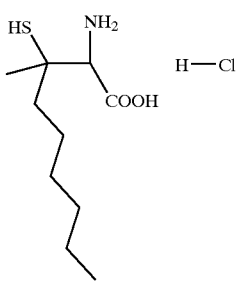

rac-2-amino-3-mercapto-3-methylnonanoic acid hydrochloride as a 6:4 threo/erythro mixture Compound 6)

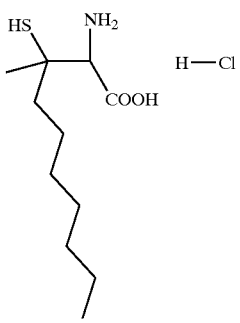

rac-2-amino-3-mercapto-3-methyldecanoic acid hydrochloride as a 6:4 threo/erythro mixture Compound 7)

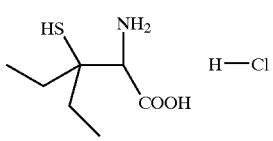

rac-2-amino-3-ethyl-3-mercaptopentanoic acid hydrochloride

Compound 8)

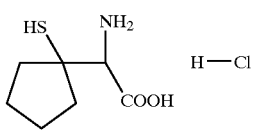

rac-amino-(1-mercaptocyclopentyl)acetic acid hydrochloride

Compound 9)

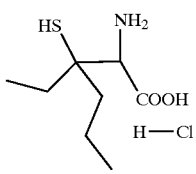

rac-amino-3-ethyl-3-mercaptohexanoic acid hydrochloride as a 1:1 threo/erythro mixture Compound 10)

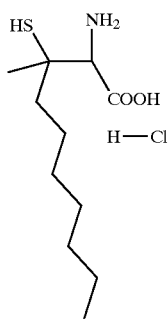

rac-threo-2-amino-3-mercapto-3-methyldecanoic acid hydrochloride

Compound 11)

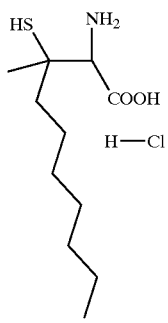

rac-erythro-2-amino-3-mercapto-3-methyldecanoic acid hydrochloride

Compound 12)

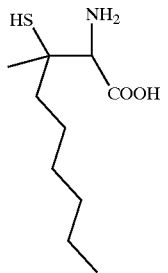

rac-threo-2-amino-3-mercapto-3-methylnonanoic acid hydrochloride

Compound 13)

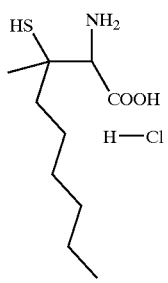

rac-erythro-2-amino-3-mercapto-3-methylnonanoic acid hydrochloride

Compound 14)

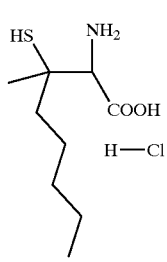

rac-threo-2-amino-3-mercapto-3-methyloctanoic acid hydrochloride

Compound 15)

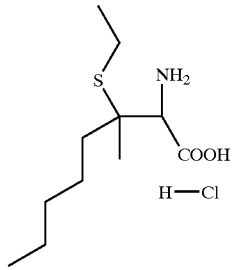

rac-2-amino-3-ethylsulfanyl-3-methyl-octanoic acid hydrochloride as a 1:1 threo/erythro mixture Compound 16)

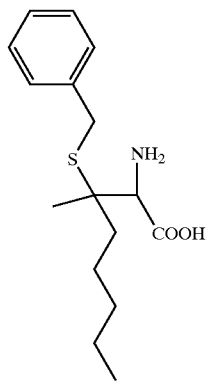

rac-threo-2-amino-3-benzylsulfanyl-3-methyl-octanoic acid hydrochloride

Compound 17)

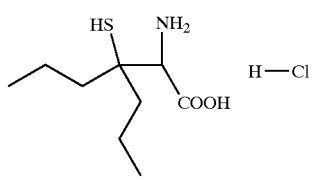

rac-2-amino-3-mercapto-3-propyl-3-hexanoic acid hydrochloride

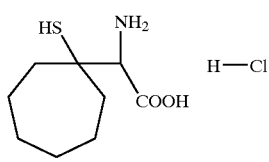

Compound 18)

rac-amino-(1-mercaptocycloheptyl)acetic acid hydrochloride

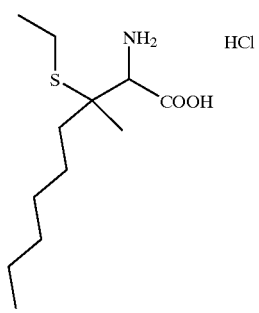

Compound 19)

rac-2-amino-3-ethylsulfanyl-3-methylnonanoic acid hydrochloride as a 6:4 threo/erythro mixture

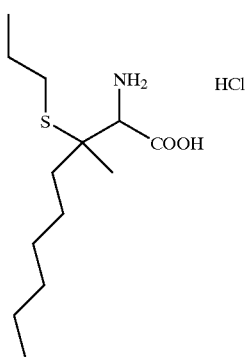

Compound 20)

rac-2-amino-3-methyl-3-propylsulfanylnonanoic acid hydrochloride as a 6:4 threo/erythro mixture

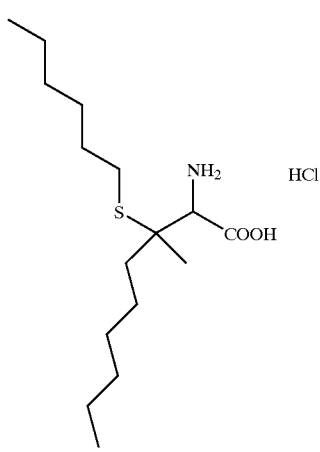

Compound 21)

rac-2-amino-3-hexylsulfanyl-3-methylnonanoic acid hydrochloride as a 6:4 threo/erythro mixture

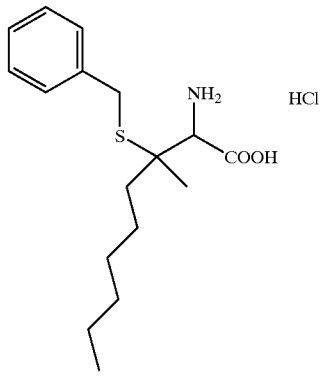

Compound 22)

rac-2-amino-3-benzylsulfanyl-3-methyl-nonanoic acid hydrochloride as a 6:4 threo/erythro mixture

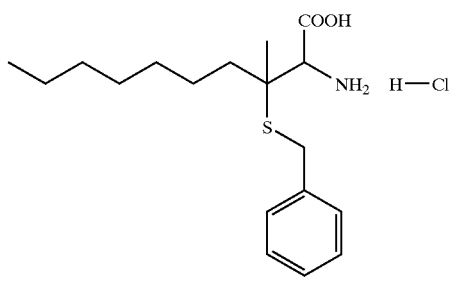

Compound 23)

rac-2-amino-3-benzylsulfanyl-3-methyldecanoic acid hydrochloride as a 6:4 threo/erythro mixture

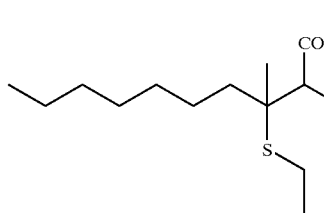

Compound 24)

rac-2-amino-3-ethylsulfanyl-3-methyldecanoic acid hydrochloride as a 6:4 threo/erythro mixture

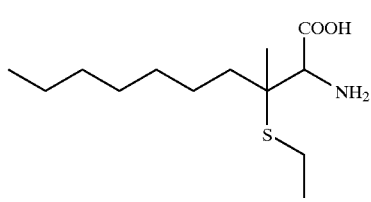

Compound 25)

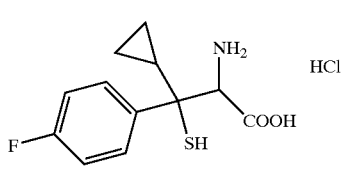

rac-2-amino-3-cyclopropyl-3-(4-fluorophenyl)-3-mercapto-propionic acid hydrochloride as a 6:4 threo/erythro mixture Compound 26)

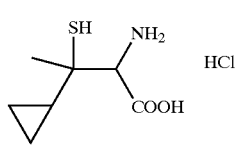

rac-2-amino-3-cyclopropyl-3-mercaptobutanoic acid hydrochloride as a 6:4 threo/erythro mixture

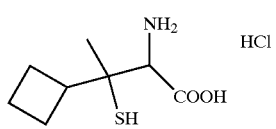

Compound 27)

rac-2-amino-3-cyclobutyl-3-mercapto-butanoic acid hydrochloride as a 6:4 threo/erythro mixture

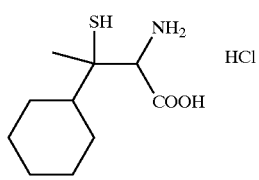

Compound 28)

rac-2-amino-3-cyclohexyl-3-mercaptobutanoic acid hydrochloride as a 6:4 threo/erythro mixture

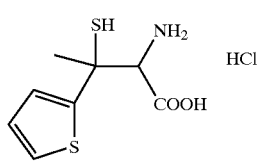

Compound 29)

rac-2-amino-3-mercapto-3-thiophen-2-yl-butanoic acid hydrochloride as a 6:4 threo/erythro mixture

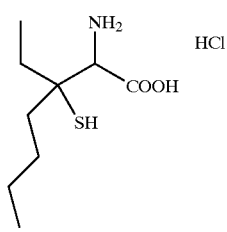

Compound 30)

rac-2-amino-3-ethyl-3-mercaptoheptanoic acid hydrochloride as a 6:4 threo/erythro mixture

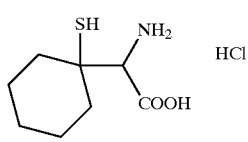

Compound 31)

rac-amino-(1-mercaptocyclohexyl)ethanoic acid hydrochloride

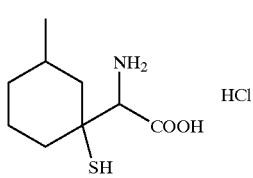

Compound 32)

rac-amino-(1-mercapto-3-methylcyclohexyl)ethanoic acid hydrochloride

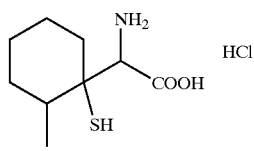

Compound 33)

rac-amino-(1-mercapto-2-methylcyclohexyl)ethanoic acid hydrochloride

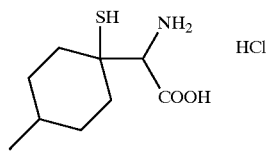

Compound 34)

rac-amino-(1-mercapto-4-methylcyclohexyl)ethanoic acid hydrochloride

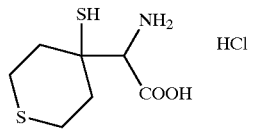

Compound 35)

rac-amino-(4-mercaptotetrahydrothiopyran-4-yl)ethanoic acid hydrochloride

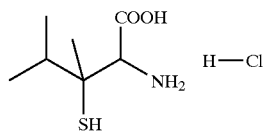

Compound 36)

rac-2-amino-3-mercapto-3,4-dimethylpentanoic acid hydrochloride as a 6:4 threo/erythro mixture

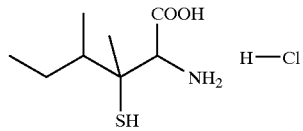

Compound 37)

rac-2-amino-3-mercapto-3,4-dimethylhexanoic acid hydrochloride as a 6:4 threo/erythro mixture

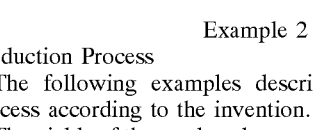

Example 2
Production Process

The following examples describe in more detail the process according to the invention.

The yields of the produced compounds are not optimized. All temperatures are uncorrected.

Silica gel 60 (0.040–0.063 mm) from E. Merck, Darmstadt was used as stationary phase for the column chromatography.

The thin-layer chromatography investigations were carried out with HPTLC precoated plates, silica gel 60 F 254, from E. Merck, Darmstadt.

The mixing ratios of the solvents for all chromatography investigations are always given in volume/volume.

The term ether denotes diethyl ether.

Unless otherwise stated, petroleum ether with a boiling point range of 50° C.–70° C. was used.

Procedure 1

Preparation of Compound 6 rac-2-amino-3-mercapto-3-methyldecanoic acid hydrochloride as a 6:4 threo/erythro mixture (product 1)

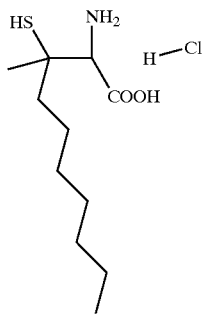

1. Glycine Ethyl Ester Hydrochloride (Product 2)

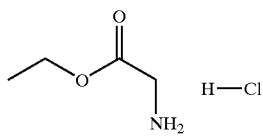

247.3 g of thionyl chloride and 130 g of glycine were added at –10° C. to 1000 ml of ethanol. After removing the ice bath a further equivalent amount of glycine was added in portions. The mixture was then stirred for 2 hours under reflux. After cooling to room temperature the excess alcohol and the thionyl chloride were removed on a rotary evaporator. Ethanol was added twice more to the white solid obtained and the ethanol was in turn removed on the rotary evaporator in order completely to remove adhering thionyl chloride. After recrystallisation from ethanol 218.6 g (90.4% of theory) of the title compound (product 2) were obtained.

2. Formylaminoacetic Acid Ethyl Ester (Product 3

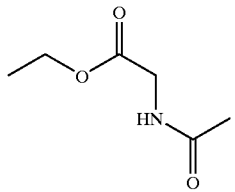

218 g of glycine ethyl ester hydrochloride (product 2) were suspended in 1340 ml of ethyl formate. 223 mg of toluenesulfonic acid were added and the mixture was heated under reflux. 178 g of triethylamine were now added dropwise to the boiling solution and the reaction solution was stirred overnight under reflux. After cooling to room temperature the precipitated ammonium chloride salt was filtered off, the filtrate was concentrated by evaporation to ca. 20% of the original volume and cooled to –5° C. The reprecipitated ammonium chloride salt was filtered off, the filtrate was reconcentrated by evaporation and distilled at 1 mbar. 184 g (90.3% of theory) of the title compound (product 3) were thereby obtained.

3. Isocyanoacetic Acid Ethyl Ester (Product 4)

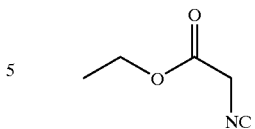

50 g of formylaminoacetic acid ethyl ester (product 3) and 104 g of diisopropylamine were added to 400 ml of dichloromethane and cooled to –3° C. 70.1 g of phosphoryl chloride in 400 ml of dichloromethane were then added dropwise and stirred for a further hour at this temperature. After removing the ice bath and allowing the temperature to rise to room temperature, the reaction solution was carefully hydrolysed with 400 ml of 20% sodium carbonate solution. After stirring for 60 minutes at room temperature 400 ml of water were added, followed by 200 ml of dichloromethane. The phases were separated and the organic phase was washed twice with in each case 100 ml of 5% $Na_2CO_3$ solution and dried over $MgSO_4$. The solvent was evaporated on a rotary evaporator and the remaining brown oil was distilled. 34.16 g (79.3% of theory) of the title compound (product 4) were thus obtained.

4. (E)- and (Z)-2-formylamino-3-methyldec-2-ene acid ethyl ester (Product 5)

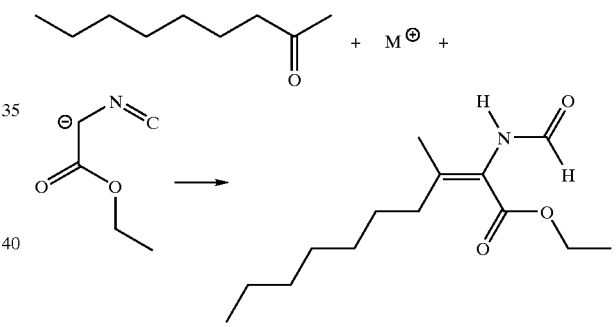

A solution of 22 g of isocyanoacetic acid ethyl ester (product 4) in 49 ml of THF was added dropwise while stirring to a suspension of 23 g of potassium tert.-butylate in 148 ml of THF at –70° C. to –60° C. The reaction mixture was stirred for a further 20 minutes, following which 27.7 g of 2-nonanone in 24 ml of THF were added dropwise at this temperature. After heating to room temperature 11.7 ml of glacial acetic acid were added. 15 minutes after addition of the glacial acetic acid (TLC check: ether:hexane 4:1) the solvent was evaporated. 300 ml of diethyl ether and 200 ml of water were then added to the residue. The organic phase was separated and the aqueous phase was washed twice with in each case 120 ml of ether. The combined organic phases were washed with 80 ml of 2N $NaHCO_3$ solution and dried over $MgSO_4$. The solvent was then evaporated. The crude product thus obtained was digested with 200 ml of n-hexane. The solid was filtered off, washed four times with in each case 80 ml of hexane, and dried in an oil pump vacuum. 34.8 g (69.9% of theory) of (E)- and (Z)-2-formylamino-3-methyldec-2-ene acid ethyl ester (product 5) (E/Z ratio: 1:1) were thus obtained as a white solid.

5. 2-formylamino-3-mercapto-3-methyldecanoic acid ethyl ester as a 6:4 threo/erythro mixture (Product 6)

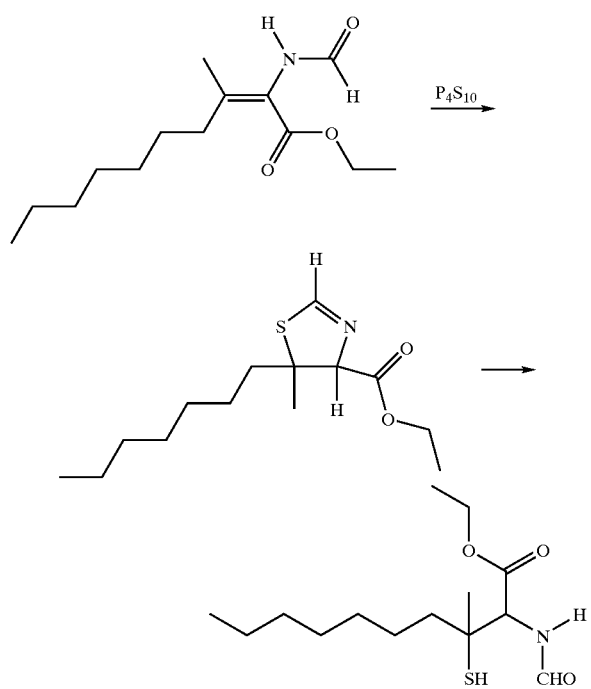

34.8 g of (E)- and (Z)-2-formylamino-3-methyldec-2-ene acid ethyl ester (product 5) (E/Z ratio: 1:1) were dissolved in 273 ml of toluene at room temperature and 6.06 g of $P_4S_{10}$ were then added. The mixture was stirred under the exclusion of moisture for 2 hours at 80° C. (TLC check: ethyl acetate:hexane 1:1). The resultant solution was then cooled to room temperature and the organic phase was freed from solvent. The crude product obtained was taken up in 300 ml of diethyl ether and 5 ml of water were added. The reaction solution was stirred overnight. The water was separated and the organic phase was dried over $MgSO_4$ and the solvent was then evaporated in vacuo. 43 g of 2-formylamino-3-mercapto-3-methyldecanoic acid ethyl ester were thus obtained as a 6:4 threo/erythro mixture (product 6) in the form of a yellow oil. This was chromatographed on silica gel with diisopropyl ether containing 1% of 25% ammonia. 30 g (76% of theory) of 2-formylamino-3-mercapto-3-methyldecanoic acid ethyl ester were thus obtained as a 6:4 threo/erythro mixture product 6) in the form of a colourless oil.

6. rac-2-amino-3-mercapto-3-methyldecanoic acid hydrochloride as a 6:4 threo/erythro mixture (Product 1)

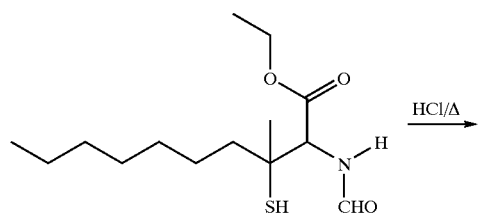

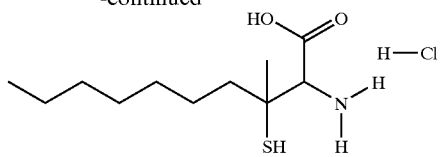

16.7 g of 2-formylamino-3-mercapto-3-methyldecanoic acid ethyl ester as a 6:4 threo/erythro mixture (product 6) were added at room temperature to 606 ml of 6N hydrochloric acid and then stirred for 24 hours under reflux (TLC check: dichloromethane:methanol:glacial acetic acid 35:5:3). After cooling to room temperature the reaction mixture was stirred further while cooling with ice. The precipitated white solid was suction filtered, washed with ether and then dried in vacuo. 13.3 g (94.9% of theory) of rac-2-amino-3-mercapto-3-methyldecanoic acid hydrochloride were thus obtained as a 6:4 threo/erythro mixture (compound 6; product 1).

Procedure 2:
Preparation of Compound 10 and
Preparation of Compound 11
 rac-threo-2-amino-3-mercapto-3-methyldecanoic acid hydrochloride (compound 10; product 7) and rac-erythro-2-amino-3-mercapto-3-methyldecanoic acid hydrochloride (compound 11; product 8).

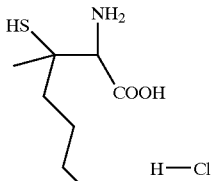
(Prod.7)

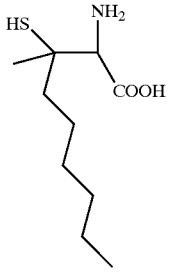
(Prod.8)

rac-threo-2-amino-3-mercapto-3-methyldecanoic acid hydrochloride (product 7) and erythro-2-amino-3-mercapto-3-methyldecanoic acid hydrochloride (product 8) were obtained as described in procedure 1, Part 1, 2, 3 and 4. Changes were made from Part 5 onwards.

5. threo-2-formylamino-3-mercapto-3-methyldecanoic acid ethyl ester (Product 9) and erythro-2-formylamino-3-mercapto-3-methyldecanoic acid ethyl ester (Product 10)

34.8 g of (E)- and (Z)-2-formylamino-3-methyldec-2-ene acid ethyl ester (product 5) (E/Z ratio: 1:1) were dissolved in 273 ml of toluene at room temperature and 6.06 g of $P_4S_{10}$ were then added. The mixture was stirred under the exclusion of moisture for 2 hours at 80° C. (TLC check: ethyl acetate:hexane 1:1). The resultant solution was then cooled to room temperature and the organic phase was freed from the solvent. The crude product obtained was taken up in 300 ml of diethyl ether and 5 ml of water were added. The mixture was stirred overnight. The water was separated and the organic phase was dried over MgSO₄ and the solvent was then evaporated in vacuo. 43 g of 2-formylamino-3-mercapto-3-methyldecanoic acid ethyl ester were thus obtained as a 6:4 threo/erythro mixture (6) in the form of a yellow oil. This was chromatographed on silica gel with diisopropyl ether containing 1% of 25% ammonia. 30 g (76% of theory) of 2-formylamino-3-mercapto-3-methyldecanoic acid ethyl ester were thus obtained as a 6:4 threo/erythro mixture (product 6) in the form of a colourless oil. This mixed fraction was rechromatographed on silica gel with diisopropyl ether containing 1% of 25% ammonia solution. 5 g (12.7% of theory) of threo-2-formylamino-3-mercapto-3-methyldecanoic acid ethyl ester (product 9) and 3.6 g (9.2% of theory) of erythro-2-formylamino-3-mercapto-3-methyldecanoic acid ethyl ester (product 10) were thus obtained.

6. rac-threo-2-amino-3-mercapto-3-methyldecanoic acid hydrochloride (Product 7) and rac-erythro-2-amino-3-mercapto-3-methyldecanoic acid hydrochloride (Product 8)

5 g of threo-2-formylamino-3-mercapto-3-methyldecanoic acid ethyl ester (product 9) were added at room temperature to 183 ml of 6N hydrochloric acid, and 3.6 g of erythro-2-formylamino-3-mercapto-3-methyldecanoic acid ethyl ester (product 10) were added at room temperature to 132 ml of 6N hydrochloric acid. The further procedure was identical. The reaction mixture was then stirred for 24 hours under reflux (TLC check: dichloromethane:methanol:glacial acetic acid 35:5:3). After cooling to room temperature the reaction mixture was stirred further while cooling with ice. The precipitated white solid was suction filtered, washed with ether and then dried in vacuo. 4.2 g (94.9% of theory) of rac-threo-2-amino-3-mercapto-3-methyldecanoic acid hydrochloride (product 7) and 3 g (94.9% of theory) of rac-erythro-2-amino-3-mercapto-3-methyldecanoic acid hydrochloride (product 8) were thus obtained.

Procedure 3
Preparation of Compound 1 rac-2-amino-3-mercapto-3-methylpentanoic acid hydrochloride as a 7:3 threo/erythro mixture (compound 1, product 11)

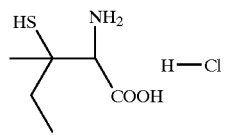

By using 2-butanone instead of 2-nonanone in procedure 1, rac-2-amino-3-mercapto-3-methylpentanoic acid hydrochloride was obtained as a 7:3 threo/erythro mixture (compound 1, product 11).

Procedure 4
Preparation of Compound 2 rac-2-amino-3-mercapto-3-methylhexanoic acid hydrochloride as a 7:3 threo/erythro mixture (compound 2, product 12)

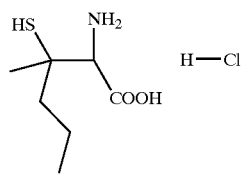

By using 2-pentanone instead of 2-nonanone in procedure 1, rac-2-amino-3-mercapto-3-methylhexanoic acid hydrochloride was obtained as a 7:3 threo/erythro mixture (product 12).

Procedure 5

Preparation of Compound 3 rac-2-amino-3-mercapto-3-methylheptanoic acid hydrochloride as a 6:4 threo/erythro mixture (compound 3, product 13)

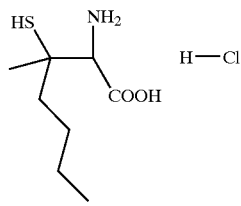

By using 2-hexanone instead of 2-nonanone in procedure 1, rac-2-amino-3-mercapto-3-methylheptanoic acid hydrochloride was obtained as a 6:4 threo/erythro mixture (compound 3, product 13).

Procedure 6

Preparation of Compound 4 rac-2-amino-3-mercapto-3-methyloctanoic acid hydrochloride as a 1:1 threo/erythro mixture (compound 4, product 14)

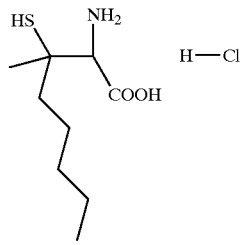

By using 2-heptanone instead of 2-nonanone in procedure 1, rac-2-amino-3-mercapto-3-methyloctanoic acid hydrochloride was obtained as a 1:1 threo/erythro mixture (compound 4, product 14).

Procedure 7

Preparation of Compound 14 rac-threo-2-amino-3-mercapto-3-methyloctanoic acid hydrochloride (compound, product 15)

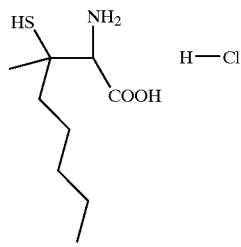

By using 2-heptanone instead of 2-nonanone in procedure 2, rac-threo-2-amino-3-mercapto-3-methyloctanoic acid hydrochloride was obtained (compound, product 15).

Procedure 8

Preparation of Compound 5 rac-2-amino-3-mercapto-3-methylnonanoic acid hydrochloride as a 6:4 threo/erythro mixture (Compound 5, Product 16)

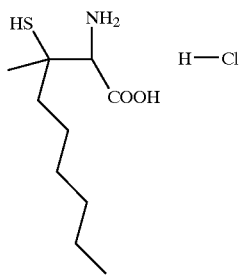

By using 2-octanone instead of 2-nonanone in procedure 1, rac-2-amino-3-mercapto-3-methylnonanoic acid hydrochloride was obtained as a 6:4 threo/erythro mixture (compound 5, product 16).

Procedure 9

Preparation of Compound 12 and Compound 13 rac-threo-2-amino-3-mercapto-3-methylnonanoic acid hydrochloride (compound 12, product 17) and rac-erythro-2-amino-3-mercapto-3-methylnonanoic acid hydrochloride (compound 13, product 18)

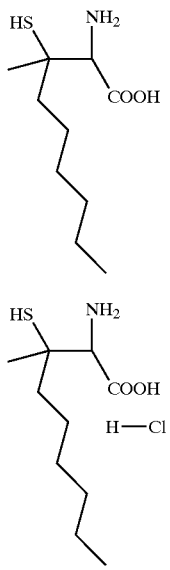

By using 2-octanone instead of 2-nonanone in procedure 2, rac-threo-2-amino-3-mercapto-3-methylnonanoic acid hydrochloride (compound 12, product 17) and rac-erythro-2-amino-3-mercapto-3-methylnonanoic acid hydrochloride (compound 13, product 18) are obtained.

Procedure 10

Preparation of Compound 7 rac-2-amino-3-ethyl-3-mercaptopentanoic acid hydrochloride (compound 7, product 19)

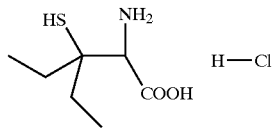

By using 3-pentanone instead of 2-nonanone in procedure 1, rac-2-amino-3-ethyl-3-mercapto-pentanoic acid hydrochloride (compound 7, product 19) was obtained.

Procedure 11

Preparation of Compound 8 rac-amino-(1-mercaptocyclopentyl)acetic acid hydrochloride (compound 8, product 20)

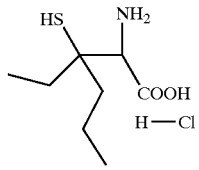

By using cyclopentanone instead of 2-nonanone in procedure 1, rac-amino-(1-mercaptocyclopentyl)acetic acid hydrochloride was obtained compound 8, product 20).

Procedure 12

Preparation of Compound 9 rac-amino-3-ethyl-3-mercaptohexanoic acid hydrochloride; as a 1:1 threo/erythro mixture (compound 9, product 21)

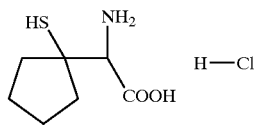

By using 3-hexanone instead of 2-nonanone in procedure 1, rac-amino-3-ethyl-3-mercaptohexanoic acid hydrochloride was obtained as a 1:1 threo/erythro mixture (compound 7, product 21).

Procedure 13

Preparation of Compound 17 rac-2-amino-3-mercapto-3-propyl-3-hexanoic acid hydrochloride (22)

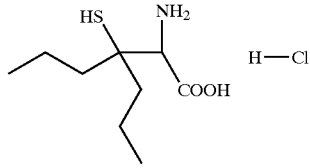

By using 4-heptanone instead of 2-nonanone in procedure 1, rac-2-amino-3-mercapto-3-propyl-3-hexanoic acid hydrochloride (22) was obtained.

Procedure 14
Preparation of Compound 18
rac-amino-(1-mercaptocycloheptyl)acetic acid hydrochloride (compound 18, product 23)

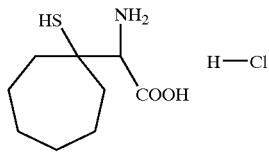

By using cycloheptanone instead of 2-nonanone in procedure 1, rac-amino-(1-mercaptocycloheptyl)acetic acid hydrochloride was obtained (compound 7, product 23).

Procedure 15
Preparation of Compound 15
rac-2-amino-3-ethylsulfanyl-3-methyloctanoic acid hydrochloride as a 1:1 threo/erythro mixture (compound 15, product 24)

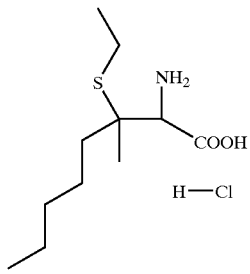

The procedure is identical to that of procedure 1; Part 1; 2 and 3. There are differences starting from Part 4.

4. (E)- and (Z)-2-formylamino-3-methyloct-2-ene acid ethyl ester (Product 25)

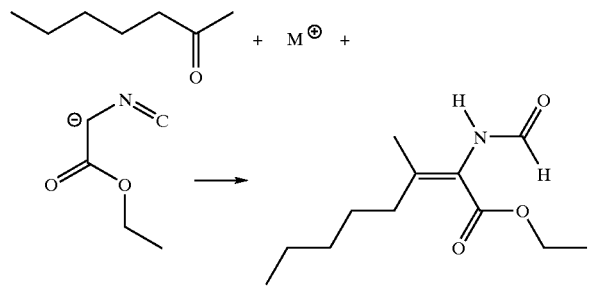

A solution of 22 g of isocyanoacetic acid ethyl ester (product 4) in 49 ml of THF was added dropwise to a suspension of 23 g of potassium tert.-butylate in 148 ml of THF at −70° C. to −60° C. while stirring. The reaction mixture was stirred for 20 minutes and 27.7 g of 2-heptanone in 24 ml of THF were then added dropwise at this temperature. After heating to room temperature 11.7 ml of glacial acetic acid were added. 15 minutes after addition of the glacial acetic acid (TLC check: ether:hexane 4:1) the solvent was evaporated. 300 ml of diethyl ether and 200 ml of water were then added to the residue. The organic phase was separated and the aqueous phase was washed twice with in each case 120 ml of ether. The combined organic phases were washed with 80 ml of 2N NaHCO$_3$ solution and dried over MgSO4. The solvent was then evaporated. The crude product thus obtained was digested with 200 ml of n-hexane. The solid was filtered off, washed four times with in each case 80 ml of hexane, and dried in an oil pump vacuum. 34.8 g (69.9% of theory) of (E)- and (Z)-2-formylamino-3-methyloct-2-ene acid ethyl ester product 25) (E/Z ratio: 1:1) were thus obtained as a white solid.

5. 3-ethylsufanyl-2-formylamino-3-methyloctanoic acid ethyl ester as a 1:1 threo/erythro mixture (Product 26)

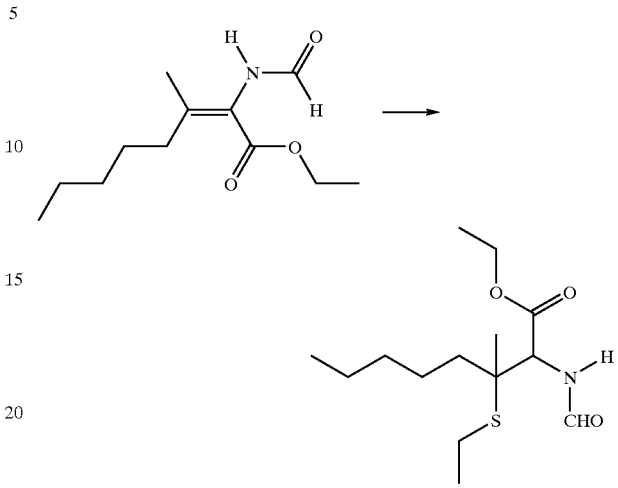

0.28 ml of butyllithium was added to 40 ml of absolute THF and the mixture was cooled to 0° C. 2.73 g of ethyl-mercaptan were now added dropwise. After stirring for 20 minutes the solution was cooled to a temperature between −40° C. and 0° C. and a solution of 1 g of (E)- and (Z)-2-formylamino-3-methyloct-2-ene acid ethyl ester (E/Z ratio: 1:1) (product 25) was then slowly added dropwise. The reaction mixture was stirred for 2 hours at this temperature, then heated to 0° C., and finally hydrolysed with 100 ml of a 5% sodium hydroxide solution. The phases were separated and the aqueous phase was extracted twice with in each case 100 ml of dichloromethane. The combined organic phases were dried over MgSO4 and the solvent was removed on a rotary evaporator. The mercaptan used in excess was separated by means of chromatography on silica gel using dichloromethane/diethyl ether (6:1) as eluent. The title compound (product 26) was thereby obtained as a colourless oil in a yield of 1.05 g (82% of theory).

6. rac-2-amino-3-ethylsulfanyl-3-methyloctanoic acid hydrochloride as a 1:1 threo/erythro mixture (Product 24)

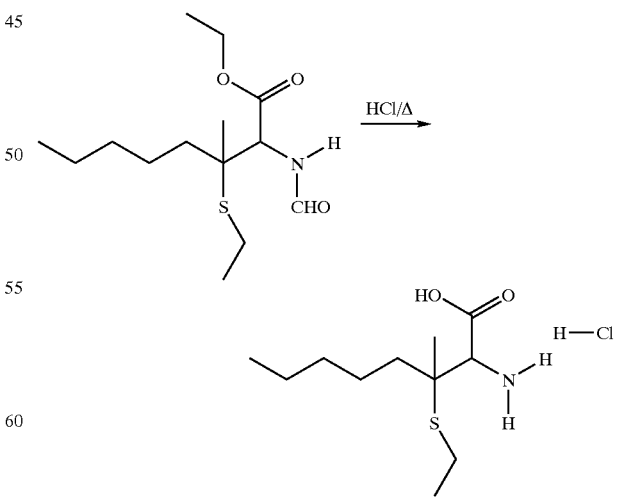

1.05 g of 3-ethylsulfanyl-3-methyloctanoic acid ethyl ester as a 1:1 threo/erythro mixture (product 26) were added at room temperature to 40 ml of 6N hydrochloric acid and then stirred for 24 hours under reflux (TLC check: dichloromethane:methanol:glacial acetic acid 35:5:3). After cooling to room temperature the reaction mixture was stirred further while cooling with ice. The precipitated white solid was suction filtered, washed with ether and then dried in vacuo. 0.8 g (94.9% of theory) of rac-2-amino-3-ethylsulfanyl-3-methyloctanoic acid hydrochloride was thus obtained as a 1:1 threo/erythro mixture (compound 15, product 24).

Procedure 16

Preparation of Compound 16 rac-threo-2-amino-benzylsulfanyl-methyloctanoic acid hydrochloride (compound 16, product 27)

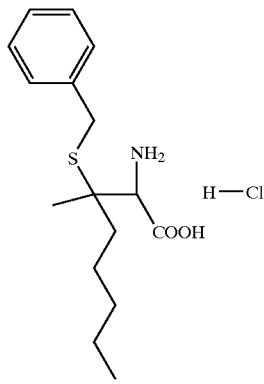

The procedure is identical to that of procedure 15; Part 1; 2, 3 and 4. There are differences from Part 5 onwards.

5. threo-3-benzylsulfanyl-2-formylamino-3-methyloctanoic acid ethyl ester (Product 28)

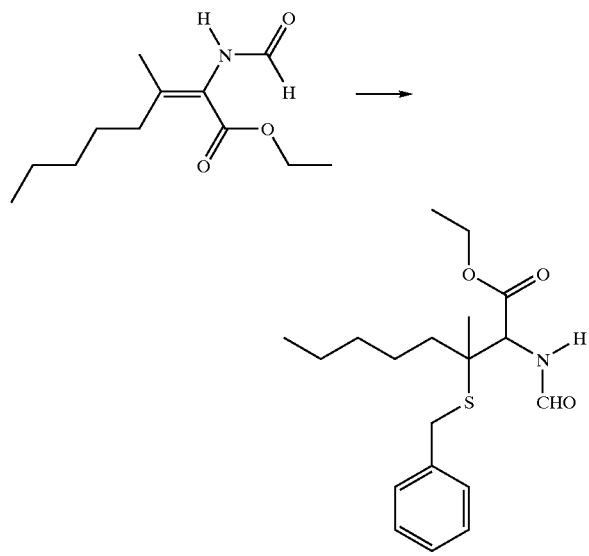

0.28 ml of n-butyllithium was added to 40 ml of absolute THF and the mixture was cooled to 0° C. 5.5 g of benzylmercaptan were now added dropwise. After stirring for 20 minutes the solution was cooled to a temperature between −40° C. and 0° C. and a solution of 1 g of (E)- and (Z)-2-formylamino-3-methyloct-2-ene acid ethyl ester (E/Z ratio: 1:1) was slowly added dropwise. The reaction mixture was stirred for 2 hours at this temperature, then heated to 0° C., and finally hydrolysed with 100 ml of a 5% sodium hydroxide solution. The phases were separated and the aqueous phase was extracted twice with in each case 100 ml of dichloromethane. The combined organic phases were dried over MgSO$_4$ and the solvent was removed on a rotary evaporator. The mercaptan used in excess was separated by means of chromatography on silica gel using dichloromethane/diethyl ether (6:1) as eluent. By crystallisation from pentane/ethanol (10:1) the title compound (product 28) was obtained as a white solid in a yield of 1.51 g (98% of theory).

6. rac-threo-2-amino-benzylsulfanyl-methyloctanoic acid hydrochloride (Product 27)

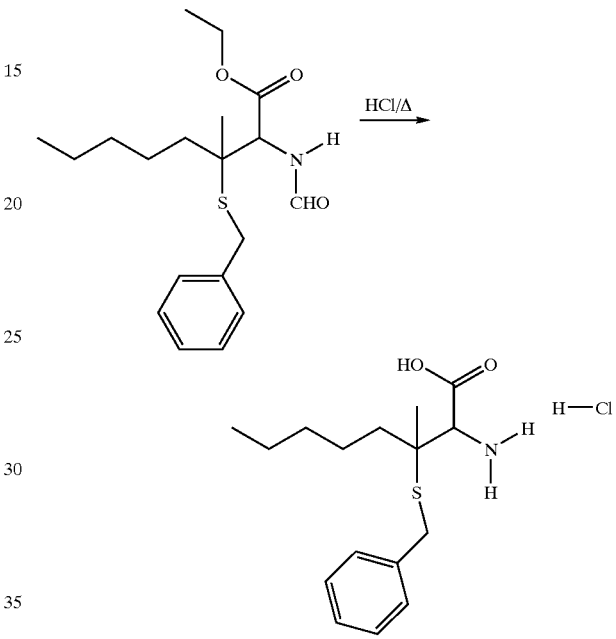

1.51 g of threo-3-benzylsulfanyl-2-formylamino-3-methyloctanoic acid ethyl ester (product 28) were added at room temperature to 40 ml of 6N hydrochloric acid and then stirred for 24 hours under reflux (TLC check: dichloromethane:methanol:glacial acetic acid 35:5:3). After cooling to room temperature the reaction mixture was stirred further while cooling with ice. The precipitated white solid was suction filtered, washed with ether and then dried in vacuo. 0.9 g (94.9% of theory) of rac-threo-2-aminobenzylsulfanylmethyloctanoic acid hydrochloride were thus obtained (compound 16, product 27).

Pharmacological Investigations

Example 3

Binding Assay

Gabapentin is used in the binding assay in order to determine the binding and affinities of the selected compounds. The affinity of the compounds according to the invention is measured via the displacement of gabapentin from its binding site. If the selected compounds can replace gabapentin from its binding site, then it may be expected that they will exhibit pharmacological properties comparable to those of gabapentin, for example as an agent to control pain or epilepsy. The compounds according to the invention exhibit a good inhibition/displacement of gabapentin in this assay. The investigated compounds furthermore exhibit in a biochemical assay an affinity for a hitherto unknown gabapentin binding site. The affinities and percentage inhibition of the compounds with respect to the gabapentin binding are given in Table 1:

TABLE 1

| Compound No. | Affinity ($IC_{50}$) nM and/or % Inhibition (Concn.) |
|---|---|
| 1 | 268 |
| 2 | 165 |
| 3 | 280 or 99.7% ($10^{-5}$ μm) |
| 4 | 186 |
| 5 | 70 |
| 6 | 199 |
| 7 | 258 |
| 8 | 151 |
| 9 | 339 or 97.5% ($10^{-5}$ μm) |
| 10 | 150 |
| 11 | 120 |
| 12 | 70 |
| 13 | 30 |
| 14 | 100 |
| 15 | 92% ($10^{-5}$ μm) |
| 16 | 1800 or 93% ($10^{-5}$ μm) |
| 17 | 2350 |
| 18 | 15% ($10^{-5}$ μm) |
| 19 | 271 |
| 20 | 3050 |
| 21 | 12400 |
| 22 | 336 |
| 23 | 91% ($10^{-5}$ μm) |
| 24 | 90% ($10^{-5}$ μm) |
| 25 | 40% ($10^{-5}$ μm) |
| 26 | 703 |
| 27 | 589 |
| 28 | 1320 |
| 29 | 30% ($10^{-5}$ μm) |
| 30 | 314 |
| 31 | 187 |
| 32 | 223 |
| 33 | 528 |
| 34 | 1004 |
| 35 | 84% ($10^{-5}$ μm) |
| 36 | 88% ($10^{-5}$ μm) |
| 37 | 196 |

Example 4
Analgesia Investigation using the Writhing Test in Mice

The antinociceptive effectiveness of the compounds according to the invention was investigated in mice using the phenylquinone-induced writhing test as modified by I. C. Hendershot and J. Forsaith, J. Pharmacol. Exp. Ther. 125, 237–240 (1959)). Male NMRI mice weighing 25–30 g were used for this purpose. Groups of 10 animals per substance dose were given intraperitoneally 10 minutes after intravenous administration of a compound according to the invention, 0.3 ml/mouse of a 0.02% aqueous solution of phenylquinone (phenylbenzoquinone, from Sigma, Deisenhofen; solution prepared by addition of 5% of ethanol and storage in a water bath at 45° C.). The animals were placed individually in observation cages. The number of pain-induced stretching movements (so-called writhing reactions=contortion of the body accompanied by stretching of the rear extremities) 5–20 minutes after administration of the phenylquinone were counted using a push-button counter. Animals that had received physiological saline solution i.v. and phenylquinone i.v. served as controls.

All substances were tested in the standard dose of 10 mg/kg. The percentage inhibition (% inhibition) of the writhing reactions due to a substance was calculated according to the following formula:

% inhibition=100−(WR treated animal/WR control×100)

All investigated compounds according to the invention exhibited an effect in the writhing test.

The results of selected writhing investigations are summarized in Table 2. Gabapentin has an $ED_{50}$ of 38 mg/kg.

TABLE 2

Analgesia investigation using the mouse writhing test

| Compound No. | Writhing Mouse i.v. $ED_{50}$ |
|---|---|
| 4 | 12 mg/kg |
| 6 | 35 mg/kg |
| 8 | 70 mg/kg |

Example 5
Formalin Test on Mice

The investigations to determine the antinociceptive action of the compounds according to the invention were carried out by the formalin test on male albino mice (NMRI, 25–35 g, Iffa Credo, Belgium).

In the formalin test the first (early) phase (0–15 minutes after the formalin injection) and the second (late) phase (15–60 minutes after the formalin injection) differ (D. Dubuisson et al., Pain, Vol. 4, pp. 161–174 (1977)). The early phase, being a direct reaction to the formalin injection, constitutes a model for acute pain, whereas the late phase is regarded as a model for persistent (chronic or inflammatory) pain (T. J. Coderre et al., Pain, Vol. 52, pp. 259–285 (1993)).

The compounds according to the invention were investigated in the second phase of the formalin test in order to obtain information on the effects of substances in chronic/inflammatory pain.

By means of a single subcutaneous formalin injection (20 μl, 1% aqueous solution) into the dorsal side of the right-hand rear paw, a nociceptive reaction was induced in unconstrained experimental animals, manifested in a noticeable licking and biting of the affected paw. The nociceptive behavior during the investigation period in the second (late) phase of the formalin test was continuously monitored by observing the animals. The pain reaction was quantified by totalling the time in seconds during which the animals continued to lick and bite the affected paw during the investigation period. After injecting substances that have an antinociceptive effect in the formalin test, the aforedescribed behavior pattern of the animals is reduced or possibly even eliminated. Corresponding to the substance tests, in which the animals had been injected with the test substance before formalin, the control animals were injected with a vehicle, i.e. solvent (e.g. 0.9% NaCl solution) before the formalin injection. The behavior of the animals after administration of the substance (n=10 per substance dose) was compared with a control group (n=10).

Based on the quantification of the pain reaction, the effect of the substance in the formalin test was determined as the change in the control in percentage terms. The $ED_{50}$ calculations were carried out by means of regression analysis. The application time before the formalin injection (intraperitoneally: 15 minutes, intravenously: 5 minutes) was chosen depending on the type of application of the compounds according to the invention.

The compounds according to the invention exhibited an inhibition of the formalin-induced nociception. The corresponding results in the formalin test on mice are summarised in Table 3. Gabapentin has an $ED_{50}$ of 79 mg/kg.

TABLE 3

Analgesia investigation in mouse formalin test

| Compound No. | Mouse Formalin Test ED$_{50}$ |
|---|---|
| 2 | 158 mg/kg (i.v.) |
| 4 | 67 mg/kg (i.v.) |
| 5 | 54 mg/kg (i.p.) |
| 6 | 66 mg/kg (i.v.) |
| 8 | 79 mg/kg (i.v.) |
| 10 | 105 mg/kg i.p. |
| 12 | 78 mg/kg i.p. |

Example 6

Bennett/Neuropathic Pain in Rats

The effectiveness in neuropathic pain was investigated using the Bennett model (Chronic Constriction Injury: Bennett and Xie, 1988, Pain 33: 87–107).

The right sciatic nerve of Sprague-Dawley rats weighing 140–160 g anaesthetised with nembutal was loosely ligatured in four places. The animals develop an hypersensitivity in the paw inervated by the damaged nerve, which after a one-week healing phase is quantified over about four weeks by means of a 4° C. cold metal plate (cold-induced allodynia). The animals are observed for a period of 2 minutes on this plate and the number of contractive reactions of the damaged paw is measured. The effect of the substance is determined at four times over a period of 1 hour (15, 30, 45 and 60 minutes after application) with reference to the baseline value before application of the substance and the resulting area under the curve (AUD) as well as the inhibition of the cold-induced allodynia at the individual measuring points is expressed as a percentage inhibition with respect to the vehicle control (AUD) and to the starting value (individual measurement points). The group size is n=10, and the significance of an anti-allodynic action is determined on the basis of the AUD values over a paired Test (* $0.05 \geq p > 0.01$;  $0.01 \geq p > 0.001$; * $p \leq 0.001$; Armitage and Berry, 1987, Stat. Methods in Medical Research, London: Blackwell Scientific Publications).

The investigated compounds according to the invention exhibited an anti-allodynic action. The results are summarized compared to gabapentin in the following Table 4.

TABLE 4

Investigation of the inhibition of neuropathic pain in rats

| Compound | Dose [mg/kg] i.p. | AUD | Change Compared to Control (%) |
|---|---|---|---|
| Gabapentin | 100 | 1940.3 ± 139.7*** | 34.5 |
| Gabapentin | 464 | 2577.8 ± 147.4*** | 47.3 |
| Compound 4 | 46.4 | 1893.1 ± 284.6*** | 32.5 |
| Compound 4 | 100 | 3603.1 ± 228.1*** | 66.9 |

Example 7

Mechanical Hyperalgesia after Paw Incision in Rats (Paw Incision Model)

1. Introduction

In this model the wound pain in the tissue surrounding an incision in the plantar side of a rear rat paw is investigated as a model of post-operative pain (Brennan, T. J., Vandermeulen, E. P., Gebhart, G. F., Pain (1996) 493–501). For this purpose the retraction latency after punctiform mechanical stimulation with an electronic von Frey filament is determined. After the paw incision a mechanical hyperalgesia develops, which remains stable over several days.

2. Material and Procedure

Paw Incision:

Male Sprague Dawley rats (bodyweight 200–300 g) are used. Under halothane anaesthesia a 1 cm-long incision is made starting 0.5 cm from the proximal end of the heel, through the skin, fascia and plantaris muscle, and closed with two stitches.

3. Experimental Procedure

The retraction threshold of the paw expressed in grams after punctiform mechanical stimulation is determined using an electronic von Frey filament (Digital Transducer Indicator Model 1601C, IITC Inc.). For this purpose the retraction threshold per measurement point is measured five times at intervals of 30 seconds and the individual median value is determined, on the basis of which the mean value of the animal cohort is in turn calculated. Ten rats were tested per group of experimental animals.

In order to investigate primary hyperalgesia, the retraction threshold is determined on the ipsilateral paw in the immediate vicinity of the incision as well as in the same position on the contralateral paw. The measurements are made twice before the operative procedure in order to determine the pre-test mean value, post-operatively immediately before administration of the substance, as well as at various times after administration of the substance (15, 30, 60, 90 and 120 minutes after application). The investigations may be carried out on substances from 2 hours up to 3 days after the operation.

4. Evaluation

The Effectiveness of a Substance is Described on the Basis of the Influence on the Retraction Threshold of the Ipsilateral Paw:

$$\% \ MPE = 100 - ((WTh_{sub} - WTh_{pre-op})/(WTh_{post-op} - WTh_{post-op}) \times 100)$$

MPE: Maximal Possible Effect $WTh_{sub}$: retraction threshold after administration of the substance $WTh_{pre-op}$: retraction threshold before the operation (pre test mean value)

$WTh_{post-op}$: retraction threshold after the operation and before administration of the substance The Mann-Whitney U Test is used to calculate the significance (p<0.05). With dose-dependent effects the ED$_{50}$ value is determined by means of a regression analysis.

5. Results

The results are summarized in Table 5:

TABLE 5

Analgesia investigation-rat paw incision

| Compound No. | Value |
|---|---|
| 6 | 27% MPE (464 mg/kg) i.p. |

Gabapentin has a value of 66% MPE at a dose of 100 mg/kg.

Gabapentin has a value of 66% MPE at a dose of 100 mg/kg.

Example 8

Parenteral Application Form 38.5 g of compound 4 are dissolved in 1 liter of water for injection at room temperature and then adjusted to isotonic conditions by addition of anhydrous glucose for injection.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound of formula I, $$R^3S\text{-}C(R^2)(R^1)\text{-}CH(NH_2)\text{-}COOH \quad \text{I}$$

wherein $R^1$ and $R^2$ is phenyl, thiophenyl, or $C_{3-8}$-cycloalkyl, in each case unsubstituted or singly or multiply substituted; or one of $R^1$ and $R^2$ is branched or unbranched $C_{1-6}$-alkyl, saturated or unsaturated, unsubstituted or singly or multiply substituted, and the other one of $R^1$ and $R^2$ is branched or unbranched $C_{3-10}$-alkyl, unsubstituted or singly or multiply substituted and $R^1$ is H; $C_{1-10}$-alkyl that is saturated or unsaturated, branched or unbranched, singly or multiply substituted or unsubstituted; $C_{3-8}$-cycloalkyl that is saturated or unsaturated, unsubstituted or singly or multiply substituted; aryl or heteroaryl, in each case unsubstituted or singly or multiply substituted; or aryl, $C_{3-8}$-cycloalkyl or heteroaryl bound by saturated or unsaturated $C_{1-3}$-alkyl and in each case unsubstituted or singly or multiply substituted;

in the form of a racemate, enantiomer, diastereomer, a mixture of the enantiomers or diastereomers thereof, physiologically compatible acidic and basic salt, a salt with a cation or a base or with anions and/or acids or in the form of a free acid or base.

2. A compound according to claim 1, wherein:

one of $R^1$ and $R^2$ is $C_{1-2}$ alkyl that is unsubstituted or singly or multiply substituted, the other of $R^1$ and $R^2$ is $C_{3-10}$-alkyl that is branched or unbranched, saturated or unsaturated, unsubstituted or singly or multiply substituted; or $R^1$ and $R^2$ is unsubstituted or singly substituted phenyl or thiophenyl; or cyclopropyl, cyclybutyl, cyclopentyl, cylcohexyl, or cycloheptyl.

3. A compound according to claim 2, wherein one of $R^1$ and $R^2$ is methyl or ethyl, and the other of $R^1$ and $R^2$ is selected from the group consisting of propyl, n-propyl, i-propyl, butyl, n-butyl, i-butyl, tert.-butyl, pentyl, hexyl, heptyl, or octyl.

4. A compound according to claim 2, wherein $R^1$ and $R^2$ are in each case independently of one another phenyl or thiophenyl which is singly or multiply substituted with $NH_2$, $OCH_3$, $CH_3$, OH, SH, $CF_3$, F, Cl, Br or I.

5. A compound according to claim 3, wherein $R^1$ is H; $C_{1-6}$-alkyl that is saturated or unsaturated, branched or unbranched, singly or multiply substituted or unsubstituted; phenyl or thiophenyl that is unsubstituted or singly substituted; or phenyl that is bound via $CH_3$, and is unsubstituted or singly substituted.

6. A compound according to claim 5, wherein $R^3$ is H; saturated $C_{1-6}$-alkyl that is unbranched and unsubstituted; or phenyl that is bound via $CH_3$, and that is unsubstituted or singly substituted.

7. A compound according to claim 6, wherein $R^3$ is methyl, ethyl, propyl, n-propyl, i-propyl, butyl, n-butyl, i-butyl, tert.-butyl, pentyl or hexyl.

8. A compound according to claim 6, wherein $R^3$ is phenyl or thiophenyl that is unsubstituted or singly substituted with $OCH_3$, $CH_3$, OH, SH, $CF_3$, F, Cl, Br or I.

9. A compound according to claim 6, wherein $R^3$ is phenyl that is bound via $CH_3$, and is unsubstituted or singly substituted with $OCH_3$, $CH_3$, OH, SH, $CF_3$, F, Cl, Br or I.

10. A compound according to claim 2, wherein one of $R^1$ and $R^2$ is unsubstituted, singly or multiply substituted $C_{1-2}$ alkyl, and the other of $R^1$ and $R^2$ is $C_{3-8}$-alkyl that is branched or unbranched, saturated or unsaturated, unsubstituted or singly or multiply substituted.

11. A compound according to claim 1, selected from the group consisting of:

2-amino-3-mercapto-3-methylhexanoic acid,
2-amino-3-mercapto-3-methylheptanoic acid,
2-amino-3-mercapto-3-methyloctanoic acid,
2-amino-3-mercapto-3-methylnonanoic acid,
2-amino-3-mercapto-3-methyldecanoic acid,
amino-3-ethyl-3-mercaptohexanoic acid,
2-amino-3-mercapto-3-methyldecanoic acid,
2-amino-3-mercapto-3-methylnonanoic acid,
2-amino-3-mercapto-3-methyloctanoic acid,
2-amino-3-ethylsulfanyl-3-methyloctanoic acid,
2-amino-3-benzylsulfanyl-3-methyloctanoic acid,
2-amino-3-mercapto-3-propyl-3-hexanoic acid,
amino-(1-mercaptocycloheptyl)acetic acid,
2-amino-3-mercapto-3-propyl-3-hexanoic acid,
2-amino-3-ethylsulfanyl-3-methylnonanoic acid,
2-amino-3-methyl-3-propylsulfanylnonanoic acid,
2-amino-3-hexylsulfanyl-3-methylnonanoic acid,
2-amino-3-benzylsulfanyl-3-methylnonanoic acid,
2-amino-3-benzylsulfanyl-3-methyldecanoic acid,
2-amino-3-ethylsulfanyl-3-methyldecanoic acid,
2-amino-3-cyclopropyl-3-mercaptobutanoic acid,
2-amino-3-cyclobutyl-3-mercaptobutanoic acid,
2-amino-3cyclohexyl-3-mercaptobutanoic acid,
2-amino-3-mercapto-3-thiophen-2-yl-butanoic acid,
2-amino-3-ethyl-3-mercaptoheptanoic acid,
2-amino-3-mercapto-3,4-dimethylpentanoic acid, and
2-amino-3-mercapto-3,4-dimethylhexanoic acid, in the form of a racemate, enantiomer, diastereomer, a mixture of the enantiomers or diastereomers thereof, physiologically compatible acidic and basic salt, a salt with a cation or a base or with anions and/or acids or in the form of a free acid or base.

12. A hydrochloride of a compound according to claim 1.

13. A pure diastereomer or enantiomer of a compound of according to claim 1.

14. A racemate of a compound according to claim 1.

15. A non-equimolar mixture of enantiomers of a compound according to claim 1.

16. A non-equimolar or equimolar mixture of diastereomers of a compound according to claim 1.

17. A pharmaceutical composition for the treatment of pain, epilepsy, migraine, hyperalgesia, allodynia, hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, a neurodegenerative disease; gastrointestinal lesions; erythromelalgic or post-poliomyelitic pain, trigeminal or post-herpes neuralgia; or as an anticonvulsant, analgesic or anxiolytic, the pharmaceutical composition comprising a compound according to claim 1, and a pharmaceutically acceptable exipient.

18. A pharmaceutical composition according to claim 17, which is for the treatment neuropathic, chronic pain, acute pain, inflammatory pain, post-operative pain, thermal hyperalgesia, mechanical hyperalgesia, allodynia, or cold-induced allodynia.

19. A pharmaceutical composition of claim 17, wherein the compound of formula I is selected from the group consisting of:

2-amino-3-mercapto-3-methylpentanoic acid,
2-amino-3-mercapto-3-methylhexanoic acid,
2-amino-3-mercapto-3-methylheptanoic acid,
2-amino-3-mercapto-3-methyloctanoic acid,
2-amino-3-mercapto-3-methylnonanoic acid,
2-amino-3-mercapto-3-methyldecanoic acid,
2-amino-3-ethyl-3-mercaptopentanoic acid,
amino-(1-mercaptocyclopentyl)acetic acid,
amino-3-ethyl-3-mercaptohexanoic acid,
2-amino-3-mercapto-3-methyldecanoic acid,
2-amino-3-mercapto-3-methylnonanoic acid,
2-amino-3-mercapto-3-methyloctanoic acid,
2-amino-3-ethylsulfanyl-3-methyloctanoic acid,
2-amino-3-benzylsulfanyl-3-methyloctanoic acid,
2-amino-3-mercapto-3-propyl-3-hexanoic acid,
amino-(1-mercaptocycloheptyl)acetic acid,
2-amino-3-mercapto-3-propyl-3-hexanoic acid,
amino-(1-mercaptocycloheptyl)acetic acid,
2-amino-3-ethylsulfanyl-3-methylnonanoic acid,
2-amino-3-methyl-3-propylsulfanylnonanoic acid,
2-amino-3-hexylsulfanyl-3-methylnonanoic acid,
2-amino-3-benzylsulfanyl-3-methylnonanoic acid,
2-amino-3-benzylsulfanyl-3-methyldecanoic acid,
2-amino-3-ethylsulfanyl-3-methyldecanoic acid,
2-amino-3-cyclopropyl-3-(4-fluorophenyl)-3-mercaptopropanoic acid,
2-amino-3-cyclopropyl-3-mercaptobutanoic acid,
2-amino-3-cyclobutyl-3-mercaptobutanoic acid,
2-amino-3-cyclohexyl-3-mercaptobutanoic acid,
2-amino-3-mercapto-3-thiophen-2-yl-butanoic acid,
2-amino-3-ethyl-3-mercaptoheptanoic acid,
amino-(1-mercaptocyclohexyl)-ethanoic acid,
amino-(1-mercapto-3-methylcyclohexyl)-ethanoic acid,
amino-(1-mercapto-2-methylcyclohexyl)-ethanoic acid,
amino-(1-mercapto-4-methylcyclohexyl)-ethanoic acid
amino-(4-mercaptotetrahydrothiopyran-4-yl)-ethanoic acid,
2-amino-3-mercapto-3,4-dimethylpentanoic acid, and
2-amino-3-mercapto-3,4-dimethylhexanoic acid,

20. A pharmaceutical composition of claim 17, comprising a hydrochloride of the compound of formula I.

21. A pharmaceutical composition of claim 17, comprising a pure diastereomer or enantiomer of the compound of formula I.

22. A pharmaceutical composition of claim 17, comprising a racemate of the compound of formula I.

23. A pharmaceutical composition of claim 17, comprising a non-equimolar of enantiomers of the compound of formula I.

24. A pharmaceutical composition of claim 17, comprising a non-equimolar or equimolar mixture of diastereomers of the compound of formula I.

25. A method for the treatment of pain, epilepsy, migraine, hyperalgesia, allodynia, hot flushes, post-menopausal symptoms, amyotropic lateral sclerosis (ALS), reflex sympathetic dystrophy (RSD), spastic paralysis, restless leg syndrome, acquired nystagmus; psychiatric or neuropathological disorders such as bipolar disorders, anxiety, panic attacks, mood fluctuations, manic behavior, depression, manic-depressive behavior; painful diabetic neuropathy, symptoms and pain due to multiple sclerosis or Parkinson's disease, a neurodegenerative disease; gastrointestinal lesions; erythromelalgic or post-poliomyelitic pain, trigeminal or post-herpes neuralgia; or as an anticonvulsant, analgesic or anxiolytic, the method comprising administering an effective amount of the pharmaceutical composition according to claim 17, to a patient in need thereof.

26. A method according to claim 25, which is for the treatment neuropathic, chronic pain, acute pain, inflammatory pain, post-operative pain, thermal hyperalgesia, mechanical hyperalgesia, allodynia, or cold-induced allodynia.

27. A process for preparing a compound according to claim 1, comprising:

deprotonating an isocyanoacetic acid ethyl ester with a base, reacting the deprotonated isocyanoacetic acid ethyl ester with a ketone of formula 2 in tetrahydrofuran, to form a (E,Z)-2-formylaminoacrylic acid ethyl ester of formula 3, reacting the (E,Z)-2-formylaminoacrylic acid ethyl ester of formula 3 with $P_4S_{10}$ in toluene, or with a mercaptan of the formula $R_3SH$ in the presence of butyllithium in toluene, to form a formylamino ethyl ester of formula 4, reacting the formylamino ethyl ester of formula 4 with an acid, producing a thioamino acid of formula 1,

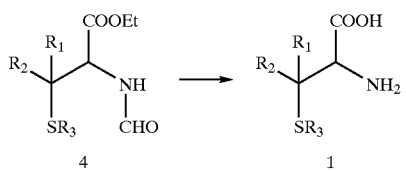

wherein R1 to R3 are as defined in claim 1, or are a corresponding radical protected with a suitable protective group.

28. A process according to claim 27, wherein isocyanoacetic acid ethyl ester is deprotonated with butyllithium, sodium hydride or potassium tert.-butylate.

29. A process according to claim 27, wherein the formylamino ethyl ester of formula 4 is reacted with hydrochloric acid.

30. A process according to claim 27, further comprising separating of diastereomers of at least one of formulae 1, 3 or 4 at a suitable stage.

31. A process according to claim 30, wherein the diastereomers are separated by means of HPLC, column chromatography or crystallization.

32. A process according to claim 27, further comprising separating enantiomers of at least one of formulae 1, 3 or 4 at a suitable stage.

33. A process according to claim 32, wherein the enantiomers are separated by means of HPLC, column chromatography or crystallization.

34. A method according to claim 17, wherein the neurodegenerative disease is selected from the group consisting of such as Alzheimer's disease, Huntington's disease, Parkinson's disease and epilepsy.

35. A method according to claim 25, wherein the neurodegenerative disease is selected from the group consisting of such as Alzheimer's disease, Huntington's disease, Parkinson's disease and epilepsy.

* * * * *